US009377463B2

(12) United States Patent
Krek et al.

(10) Patent No.: US 9,377,463 B2
(45) Date of Patent: Jun. 28, 2016

(54) METHOD FOR BIOMARKER AND DRUG-TARGET DISCOVERY FOR PROSTATE CANCER DIAGNOSIS AND TREATMENT AS WELL AS BIOMARKER ASSAYS DETERMINED THEREWITH

(71) Applicants: ETH ZURICH, Zurich (CH); Kantonsspital St. Gallen, St. Gallen (CH)

(72) Inventors: Wilhelm Krek, Herrliberg (CH); Igor Cima, Torre-Blenio (CH); Rudolf Aebersold, Zurich (CH); Ralph Schiess, Zurich (CH); Thomas Cerny, St. Gallen (CH); Silke Gillessen, St. Gallen (CH)

(73) Assignees: ETH ZURICH, Zurich (CH); Kantonsspital St. Gallen, St. Gallen (CH)

( * ) Notice: Subject to any disclaimer, the term of this patent is extended or adjusted under 35 U.S.C. 154(b) by 0 days.

(21) Appl. No.: 14/311,412

(22) Filed: Jun. 23, 2014

(65) Prior Publication Data
US 2014/0322732 A1 Oct. 30, 2014

Related U.S. Application Data

(63) Continuation of application No. 12/992,542, filed as application No. PCT/EP2009/055698 on May 12, 2009, now abandoned.

(30) Foreign Application Priority Data

May 14, 2008 (EP) .................................... 08008910

(51) Int. Cl.
  *G01N 33/53* (2006.01)
  *G01N 33/574* (2006.01)
  *G01N 33/68* (2006.01)

(52) U.S. Cl.
  CPC .... *G01N 33/57434* (2013.01); *G01N 33/57407* (2013.01); *G01N 33/6848* (2013.01)

(58) Field of Classification Search
  None
  See application file for complete search history.

(56) References Cited

U.S. PATENT DOCUMENTS

| 2004/0023306 A1 | 2/2004 | Aebersold et al. |
| 2007/0099209 A1 | 5/2007 | Clarke et al. |
| 2009/0163414 A1 | 6/2009 | Castronovo et al. |

FOREIGN PATENT DOCUMENTS

| EP | 0180687 A1 | 5/1986 |
| JP | 2006507476 A | 3/2006 |
| WO | 2006/002378 A2 | 1/2006 |
| WO | 2007/039550 A2 | 4/2007 |

OTHER PUBLICATIONS

Wolff et al (Eur J Cancer, 1995, 31A(3): 339-341).*
Balwir Matharoo-Ball, et al., "Clinical proteomics: Discovery of cancer biomarkers using mass spectrometry and bioinformatics approaches—A prostate cancer perspective", Vaccine, Oct. 2007, pp. B110-B121, vol. 25S.
N. Leigh Anderson, et al., "The Human Plasma Proteome", Molecular & Cellular Proteomics, Apr. 2004, pp. 311-326, vol. 3, No. 4.
Jianru Stah-Zeng, et al., "High Sensitivity Detection of Plasma Proteins by Multiple Reaction Monitoring of N-Glycosites", Molecular & Cellular Proteomics, Oct. 2007, pp. 1809-1817, vol. 6, No. 10.
Euan Murray, et al., "Microarray-Formatted Clinical Biomarker Assay Development Using Peptide Aptamers to Anterior Gradient-2", Biochemistry, Dec. 2007, pp. 13742-13751, vol. 46.
Daniel C. Liebler, "Shotgun mass spec goes independent", Nature Methods, Oct. 2004, pp. 16-17, vol. 1, No. 1.

(Continued)

*Primary Examiner* — Sean Aeder
(74) *Attorney, Agent, or Firm* — Sughrue Mion, PLLC

(57) ABSTRACT

The invention relates to a method for the determination of a cancer diagnostic/therapeutic biomarker assay and drug-targets including the following steps: (a) identification of potential candidate protein/peptide biomarkers and drug-targets based on the measurement of protein/peptide constituent concentrations in tissue sample proteomes as well as serum, plasma or any other derivatives of blood, or blood itself sample proteomes derived from healthy non-human mammalian individuals as well as from cancerous non-human mammalian individuals and qualitatively selecting as potential candidate protein/peptide biomarkers those which show a pronounced differential behavior between healthy and cancerous sample proteomes; (b) optional verification of the potential candidate protein/peptide biomarkers as identified in step (a) by quantitative mass spectrometric measurement of the potential candidate protein biomarkers in serum, plasma or any other derivatives of blood, or blood itself sample proteomes derived from healthy non-human mammalian individuals as well as from cancerous non-human mammalian individuals and selecting as candidate protein/peptide biomarkers those which show a mass-spectrometrically measurable quantitative differential behavior between healthy and cancerous sample proteomes; (c) validation of the candidate protein/peptide biomarkers as identified in step (a), or as optionally verified in step (b), by mass spectrometric measurement and/or antibody-based assays such as an Enzyme-Linked Immunosorbent Assay (ELISA) determination of the candidate protein biomarkers in serum, plasma or any other derivatives of blood, or blood itself sample proteomes derived from healthy human individuals as well as from cancerous human individuals and selecting as protein/peptide biomarkers those which show a mass-spectrometrically measurable and/or antibody-based assay detectable differential behavior between healthy and cancerous sample proteomes; (d) application of statistical methods to uncover single or groups of protein/peptide biomarkers as validated in step (c) as signatures for the detection of patients with cancer. The invention furthermore relates to specific biomarker assays for the highly reliable diagnosis of cancer, specifically of localized or non-localized prostate cancer, using human serum, plasma or any other derivatives of blood, or blood itself.

13 Claims, 4 Drawing Sheets

(56) References Cited

OTHER PUBLICATIONS

Figure 1:
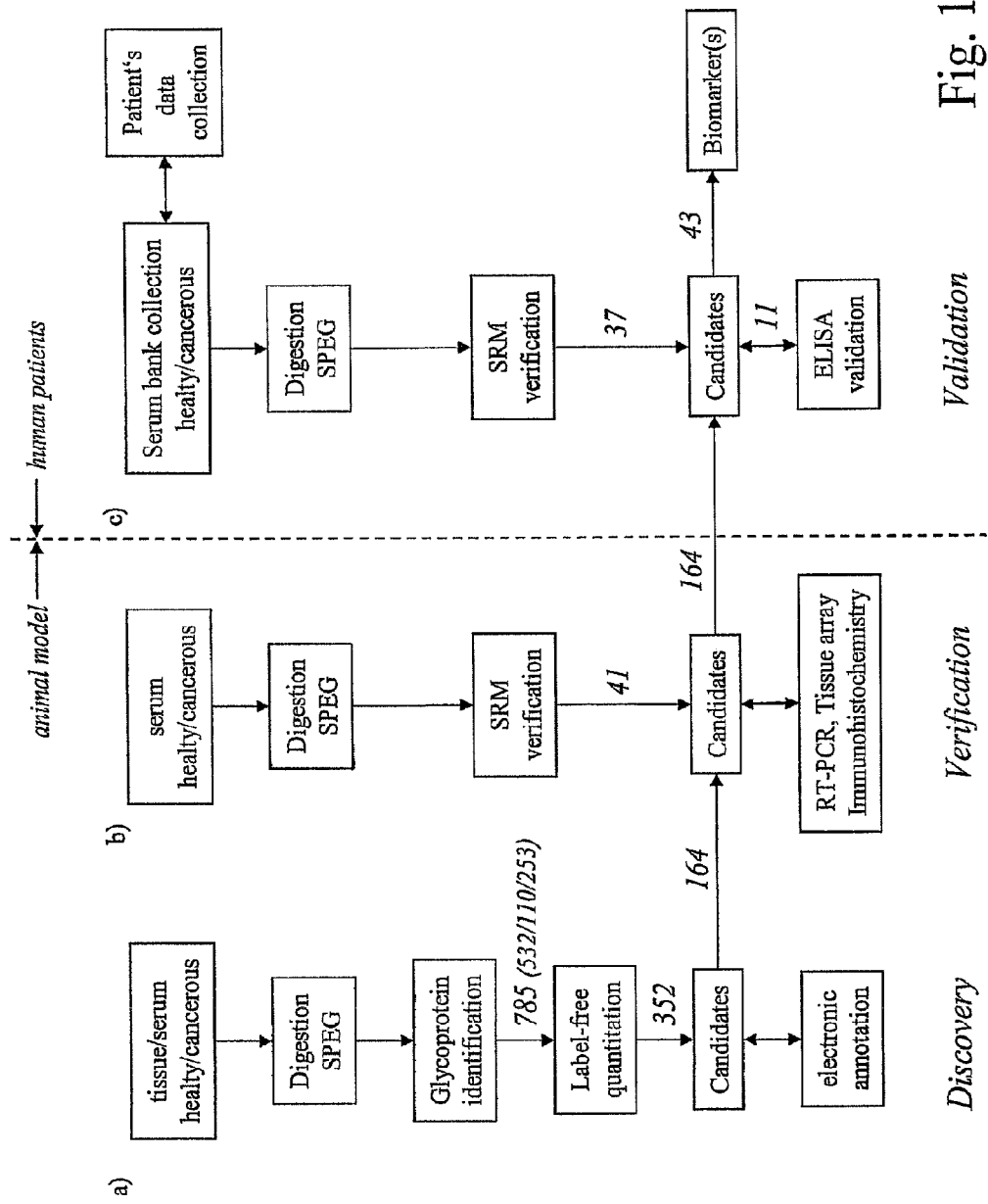

Edward M. Marcotte, "How do shotgun proteomics algorithms identify proteins", Nature Biotechnology, Jul. 2007, pp. 755-757, vol. 25, No. 7.

Alexey I. Nesvizhskii, et al., "Protein Identification by Tandem Mass Spectrometry and Sequence Database Searching", Methods in Molecular Biology, 2007, pp. 87-119, vol. 367.

Jean W. Lee, et al., "Biomarker Assay Translation from Discovery to Clinical Studies in Cancer Drug Development: Quantification of Emerging Protein Biomarkers", Advances in Cancer Research, Jan. 2007, pp. 269-298, vol. 96.

Amelie M. Lutz, et al., "Cancer Screening: A Mathematical Model Relating Secreted Blood Biomarker Levels to Tumor Sizes", PLOS Medicine, Aug. 2008, vol. 5, Issue 8.

Kuvibidila et al. (J Lab Clin. Med, 2004, 144(4):176-182).

Hara et al (Oncol. Rep, 2002, 9(6): Abstract).

Shafer et al (Prostate, 2007, 67(3): 255-267).

Etzioni et al (Nature Review, 2003, 3: internet pp. 1-10).

Mercer (Immunol Ser. 1990, 53:39-54).

Matsuo et al (Arthritis Research & Therapy, 2006, 8(6): 1-13).

Fedarko et al (Clinical Cancer Research, 2001,7(12):4060-4066).

\* cited by examiner

Discrimination between benign prostate hyperplasia (BPH, n=15) and localized prostate cancer (locPCa, n=16)

A) The following biomarkers positively contributed to the core for the discrimination between BPH and locPCa

| a | AOC3 (SRM) ASPN (SRM) VTN (SRM) |
|---|---|
| Accuracy | 81% |
| Sensitivity | 81% |
| Specificity | 80% |

| b | LOX (SRM) ASPN (SRM) VTN (SRM) |
|---|---|
| Accuracy | 84% |
| Sensitivity | 88% |
| Specificity | 80% |

| c | PGCP (SRM) ASPN (SRM) VTN (SRM) |
|---|---|
| Accuracy | 81% |
| Sensitivity | 81% |
| Specificity | 80% |

| d | PSAP (SRM) ASPN (SRM) VTN (SRM) |
|---|---|
| Accuracy | 81% |
| Sensitivity | 100% |
| Specificity | 60% |

| e | THBS1 (SRM) ASPN (SRM) VTN (SRM) |
|---|---|
| Accuracy | 80% |
| Sensitivity | 81% |
| Specificity | 79% |

B) The following biomarkers positively contributed to the core including PSA for the discrimination between BPH and locPCa

| a | AOC3 (SRM) ASPN (SRM) VTN (SRM) PSA (ELISA) |
|---|---|
| Accuracy | 90% |
| Sensitivity | 88% |
| Specificity | 93% |

| b | CFH (SRM) ASPN (SRM) VTN (SRM) PSA (ELISA) |
|---|---|
| Accuracy | 87% |
| Sensitivity | 88% |
| Specificity | 87% |

| c | CLU (SRM) ASPN (SRM) VTN (SRM) PSA (ELISA) |
|---|---|
| Accuracy | 90% |
| Sensitivity | 88% |
| Specificity | 93% |

| d | KIT (SRM) ASPN (SRM) VTN (SRM) PSA (ELISA) |
|---|---|
| Accuracy | 90% |
| Sensitivity | 88% |
| Specificity | 93% |

| e | LOX (SRM) ASPN (SRM) VTN (SRM) PSA (ELISA) |
|---|---|
| Accuracy | 90% |
| Sensitivity | 88% |
| Specificity | 93% |

| f | TFRC (SRM) ASPN (SRM) VTN (SRM) PSA (ELISA) |
|---|---|
| Accuracy | 90% |
| Sensitivity | 88% |
| Specificity | 93% |

| g | THBS1 (SRM) ASPN (SRM) VTN (SRM) PSA (ELISA) |
|---|---|
| Accuracy | 90% |
| Sensitivity | 88% |
| Specificity | 93% |

| h | GAL3BP (SRM) ASPN (SRM) VTN (SRM) PSA (ELISA) |
|---|---|
| Accuracy | 84% |
| Sensitivity | 75% |
| Specificity | 93% |

| i | GOLPH2 (SRM) ASPN (SRM) VTN (SRM) PSA (ELISA) |
|---|---|
| Accuracy | 87% |
| Sensitivity | 81% |
| Specificity | 93% |

Fig. 3

Discrimination between benign prostate hyperplasia (BPH, n=35) and localized prostate cancer (locPCa, n=41)

Discrimination between localized prostate cancer (locPCa, n=16) and metastatic prostate cancer (metPCa, n=21)

C) The following biomarkers positively contributed to the core for the discrimination between BPH and locPCa using binary logistic regression.

D) The following biomarkers positively contributed to the core for the discrimination between locPCa and metPCa a)
| PSA (ELISA) |
| OLFM4 (SRM) |
| HYOU1 (SRM) |
| ASPN (SRM) |
| CTSD (SRM) |

| Accuracy | 87% |
| Sensitivity | 90% |
| Specificity | 83% | b)
| PSA (ELISA) |
| HYOU1 (SRM) |
| ASPN (SRM) |
| OLFM4 (SRM) |

| Accuracy | 83% |
| Sensitivity | 83% |
| Specificity | 83% | c)
| PSA (ELISA) |
| ASPN (SRM) |
| CTSD (SRM) |
| OLFM4 (SRM) |

| Accuracy | 80% |
| Sensitivity | 83% |
| Specificity | 77% | d)
| PSA (ELISA) |
| HYOU1 (SRM) |
| CTSD (SRM) |
| ASPN (SRM) |

| Accuracy | 78% |
| Sensitivity | 76% |
| Specificity | 80% | e)
| PSA (ELISA) |
| HYOU1 (SRM) |
| CTSD (SRM) |
| OLFM4 (SRM) |

| Accuracy | 83% |
| Sensitivity | 85% |
| Specificity | 80% | a)
| PSAP (SRM) |
| ASPN (SRM) |
| CTSD (SRM) |
| VTN (SRM) |
| THBS1 (ELISA) |
| GALNTL4 (SRM) |

| Accuracy | 100% |
| Sensitivity | 100% |
| Specificity | 100% | b)
| CEACAM1 (ELISA) |
| ASPN (SRM) |
| CTSD (SRM) |
| VTN (SRM) |
| THBS1 (ELISA) |
| GALNTL4 (SRM) |

| Accuracy | 100% |
| Sensitivity | 100% |
| Specificity | 100% | c)
| EFNA5 (SRM) |
| ASPN (SRM) |
| CTSD (SRM) |
| VTN (SRM) |
| THBS1 (ELISA) |
| GALNTL4 (SRM) |

| Accuracy | 100% |
| Sensitivity | 100% |
| Specificity | 100% | d)
| GSPT1 (SRM) |
| ASPN (SRM) |
| CTSD (SRM) |
| VTN (SRM) |
| THBS1 (ELISA) |
| GALNTL4 (SRM) |

| Accuracy | 100% |
| Sensitivity | 100% |
| Specificity | 100% | e)
| HYOU1 (SRM) |
| ASPN (SRM) |
| CTSD (SRM) |
| VTN (SRM) |
| THBS1 (ELISA) |
| GALNTL4 (SRM) |

| Accuracy | 100% |
| Sensitivity | 100% |
| Specificity | 100% | f)
| KIT (SRM) |
| ASPN (SRM) |
| CTSD (SRM) |
| VTN (SRM) |
| THBS1 (ELISA) |
| GALNTL4 (SRM) |

| Accuracy | 100% |
| Sensitivity | 100% |
| Specificity | 100% |

Fig. 3

METHOD FOR BIOMARKER AND DRUG-TARGET DISCOVERY FOR PROSTATE CANCER DIAGNOSIS AND TREATMENT AS WELL AS BIOMARKER ASSAYS DETERMINED THEREWITH

CROSS-REFERENCE TO RELATED APPLICATIONS

This is a Continuation Application of U.S. application Ser. No. 12/992,542 filed Nov. 12, 2010, which is a National Stage of International Application No. PCT/EP2009/055698, filed May 12, 2009, which claims priority from European Patent Application No. 08 008 910.5, filed May 14, 2008, the contents of all of which are incorporated herein by reference in their entirety.

TECHNICAL FIELD

The present invention relates to the field of methods for the determination of biomarker assays and/or drug-targets for the diagnosis of cancer and its treatment and/or prognosis, specifically of prostate cancer, be it localized or non-localized prostate cancer. A further object of the present invention is to propose specific biomarker assays for these diagnostic purposes and/or patient stratification as well as methods for diagnosis using these specific biomarker assays.

BACKGROUND OF THE INVENTION

The diagnosis and treatment of prostate cancer, despite decennial research efforts, are still a major challenge in the clinics. Prostate cancer progression is unfortunately silent, and an early detection of faster progressing and potentially dangerous lesions is crucial for the patient's health, since complete remission and cure from the disease is possible only at early stages of the disease.

The best noninvasive diagnostic test available for prostate cancer is the detection of the Prostate Specific Antigen (PSA) in the blood coupled with digital rectal examination (DRE). PSA is a protein produced by the epithelial cells of the prostate gland. PSA is also known as kallikrein III, seminin, semenogelase, γ-seminoprotein and P-30 antigen and it is a 34 kD glycoprotein present in small quantities in the serum of normal men, and is often elevated in the presence of prostate cancer and in other prostate disorders. A blood test to measure PSA coupled with DRE is the most effective test currently available for the early detection of prostate cancer. Higher-than-normal levels of PSA are associated with both localized (loc) and metastatic (met) prostate cancer (CaP).

The diagnostic accuracy of PSA alone is only around 60% and the methodology has major drawbacks in specificity (too many false positives cases that undergo unneeded prostate biopsy or surgery). Indeed PSA levels can be also increased by prostate infection, irritation, benign prostatic hypertrophy (enlargement) or hyperplasia (BPH), and recent ejaculation, producing a false positive result.

A reliable and non-invasive diagnostic/prognostic procedure is thus still lacking, even tough novel methodologies based on the simultaneous measurement of various parameters (e.g. free and total PSA) are emerging as tools to increase the overall diagnostic accuracy. Most PSA in the blood is bound to serum proteins. A small amount is not protein bound and is called free PSA. In men with prostate cancer the ratio of free (unbound) PSA to total PSA is decreased. The risk of cancer increases if the free to total ratio is less than 25%. The lower the ratio, the greater the probability of prostate cancer. However, both total and free PSA increase immediately after ejaculation, returning slowly to baseline levels within 24 hours, and also other mechanisms not related to CaP can influence the free to total PSA ratio.

Similar to diagnosis, treatment and/or prognosis of prostate cancer remains a major challenge due to heterogeneity of the disease. Although multiple mechanisms of prostate cancer have been suggested, the lack of suitable signatures able to stratify patients and key target proteins for therapeutic intervention cures are still not within reach.

SUMMARY OF THE INVENTION

The object of the present invention is therefore to provide an improved method for the determination of biomarker assays and/or drug-targets for diagnosis, prognosis, treatment as well as for monitoring of treatment of cancer, and/or for the stratification of patients, specifically of prostate cancer, be it localized or non-localized prostate cancer. It should be noted that from a principle point of view the proposed method is not limited to cancer but can be applied to any kind of human or animal disease or dysfunction. From a practical point of view the only limitation can sometimes be that a model system should be available which can be used for the translational approach as described below.

It should be noted that not only candidates from a mouse (or generally animal, e.g. non-human model) are part of the invention. Potential marker candidates can be determined from a variety of sources, including also human tissue, proximal fluids, animal models cell lines, data mining etc.

There is however a rather distinctive advantage of the animal model, in the more general context of a systems biology approach to biomarker discovery. Assuming that in different cancers (that affect different tissues) cellular networks are perturbed. Assuming further that different manifestations of cancer can have the same or overlapping perturbations, an animal such as a mouse model allows to specifically apply one perturbation in isolation or defined combinations of perturbations to determine how the target tissue reacts to this perturbation. If one then furthermore assumes that some of the proteins that constitute this response, (either direct effects of the perturbation, e.g. loss of phosphopeptides if a kinase is deleted or mutated) or compensatory effects leave specific fingerprints in the target tissue, some of these fingerprints are detectable in serum using the methods we describe here. A distinctive feature of a genetically defined mouse model allows to define changes associated with a specific gene mutation (in our case e.g. PTEN) that we know is mutated also in human cancer and thus immediately suggests a subclass of patients to be looked at and treated (personalized medicine). In planning clinical trials it is often important to have solid knowledge of the prevalence and frequency of molecular marker species in the diseased population. Those patients with a high likelihood of good response may be selected in a so called patient stratification process. Based on this information the size of the available cohort can be estimated for a given strict marker profile. Retrospective studies in archived tissues e.g. allow determining those parameters fast and early before the design for the clinical phase has to be fixed and committed.

A further object of the present invention is to propose specific biomarker assays for these diagnostic/therapeutic/monitoring/prognostic/patient stratification purposes as well as methods for diagnosis/therapy/monitoring/prognosis/patient stratification using these specific biomarker assays.

The present invention according to a first aspect thus relates to a method for the determination of a cancer (or generally speaking disease/dysfunction) diagnostic/therapeutic/monitoring/prognostic/patient stratification biomarker assay including the following steps:

(a) identification of potential candidate protein/peptide biomarkers based on the measurement of protein/peptide constituent concentrations (abundances) in tissue sample proteomes as well as sample proteomes of serum, plasma or any other derivatives of blood, or blood itself derived from healthy non-human mammalian individuals as well as from cancerous non-human mammalian individuals and qualitatively selecting as potential candidate protein/peptide biomarkers those which show a pronounced differential behaviour between healthy and cancerous sample proteomes. As pointed out above, in this step not necessarily non-human samples have to be used, also human sources can be used for this step such as human tissue, proximal fluids etc.

This step can optionally be followed by step (b): verification of the potential candidate protein/peptide biomarkers as identified in step (a) by quantitative mass spectrometric measurement of the potential candidate protein biomarkers in sample proteomes of serum, plasma or any other derivatives of blood, or blood itself derived from healthy non-human mammalian individuals as well as from cancerous non-human mammalian individuals and selecting as candidate protein/peptide biomarkers those which show a mass-spectrometrically measurable quantitative differential behaviour between healthy and cancerous sample proteomes. Of course mass spectroscopy is just one and indeed the preferred way of measurement in this verification step. Also different methods for example using an affinity reagents, can be used in a way similar or identical to the one that has finally to be used for the diagnosis/prognosis/therapy.

Then follows a step (c): validation of the candidate protein/peptide biomarkers as identified in step (a), or as optionally verified in step (b), by mass spectrometric measurement and/or antibody-based determination of the candidate protein biomarkers in sample proteomes of serum, plasma or any other derivatives of blood, or blood itself derived from healthy human individuals as well as from cancerous human individuals and selecting as protein/peptide biomarkers those which show a mass-spectrometrically measurable and/or affinity reagent-based assay, preferably antibody-based assay detectable differential behaviour between healthy and cancerous sample proteomes;

(d) application of statistical methods to uncover single or groups of protein/peptide biomarkers as validated in step (c) as signatures for the detection of patients with cancer.

Preferably, the affinity reagent-based determination is, as mentioned above, an antibody-based determination method/assay, and is for example selected to be an Enzyme-Linked Immunosorbent Assay (ELISA) or a Multiplex Bead Array Assay or other methodologies aiming at measuring a particular protein concentration.

As mentioned above, the method can not only be applied for the determination of cancer biomarker systems but also to the determination of biomarker systems for other kinds of diseases or dysfunctions of an organism. In these cases in the above methods (and also in the discussion further below of the specification) the expression "cancerous" (for example for the sample) is essentially to be replaced by an expression "diseased" or "dysfunctional".

One of the gists of the present invention is therefore the concept to increase the accuracy of the non-invasive diagnostic procedure for the detection of (prostate) cancer on the one hand, and to identify new therapeutical/imaging targets used in the clinical practice. We have established a protocol for (prostate) cancer biomarkers and/or drug-targets identification, which is summarized in FIG. 1, which will be discussed in more detail further below. This approach is based on three major aspects:

(I) a translational approach based on the initial identification of candidate biomarkers and/or drug-targets, in vivo using a defined genetic mouse model and subsequent validation in human clinical samples;

(II) cutting edge mass spectrometry-based methodologies and bioinformatics methods established in our lab for the isolation, identification and quantitation of N-linked glycoproteins followed by (III) multivariate statistical methods to uncover particular signatures for the detection of patients with prostate cancer.

According to a first preferred embodiment of the proposed method, it is applied to the diagnosis of prostate cancer. To this end, the cancerous sample proteomes are selected to be sample proteomes of individuals with prostate cancer. Furthermore the tissue samples are prostate tissue samples, wherein these can be samples with localized or non-localized prostate cancer. Correspondingly the derived protein/peptide biomarkers are selected to be diagnostic of prostate cancer, can be used for the therapy of prostate cancer or for the monitoring of the therapy of prostate cancer.

According to a further embodiment of the proposed method, in step (a) proteins derived from the sample proteomes are selected to be exclusively glycoproteins, preferably N-linked glycoproteins, as these constitute a sub proteome which is highly relevant in the context of cancer drug-target and biomarker discovery.

Preferably in a first step of this step (a) the proteome of the corresponding sample is digested, preferably by using trypsin and/or Lys C (other digestive systems however being possible), and subsequently extracted using solid-phase extraction (preferably using the method SPEG as will be discussed in more detail below). The determined biomarkers are correspondingly preferred to be N-linked glycoproteins and/or peptide fragments thereof.

In principle it would be possible to use cell culture systems at least for step (a) and specifically for the tissue samples thereof. However, in order to mimic more closely the complexity of a human disease or dysfunction it is preferred to select the samples to be derived from in vivo sources, and most preferably the non-human mammalian individuals are selected to be mice, and preferably a murine prostate tissue for the samples in step (a) is perfused for complete removal of blood from the prostate tissue prior to the analysis and/or further treatment of the proteome (in case of other diseases or dysfunctions the corresponding tissue or organ can be treated analogously).

As already pointed out above, for several reasons animal models are preferred. The three main points for this preference are as follows:

the samples are homogeneous, i.e. the individuals from which the samples originate are genetically identical and have the same lesion the lesion corresponds to a lesion observed in human cancer and thus accurately models tumor development reproducible: very similar samples can be prepared over and over which is not possible in humans defined perturbation. In humans we have no control over the perturbations that lead to cancer. In animal models single or a combination of perturbations can be applied in a tissue specific and time specific manner.

After the mere identification of proteins/fragments thereof within step (a), preferably only those proteins/fragments thereof selected which show a well distinguishable differential behaviour between healthy and cancerous sample sources. To this end, the differential behaviour of the measured signals (differential abundance) is observed and only those signals (corresponding to specific protein/fragments thereof) which showed sufficient differential behaviour will be selected for the next step for further evaluation.

Differential behaviour can either be a situation, in which a specific signal is sufficiently increased/decreased when comparing the healthy with the cancerous samples signals, it can however also be a situation, in which there is no signal in the cancerous or the healthy sample signals, and a clearly detectable signal in the healthy or the cancerous sample signals, respectively. According to a preferred embodiment therefore, the selection criteria for the determination of the presence of sufficient differential behaviour in step (a) are selected from the following group:
biomarkers regulated in prostate tissue and serum; potential biomarkers regulated in prostate tissue and detected in serum; potential biomarkers regulated in prostate tissue and secreted; potential biomarkers exclusively detected in prostate tissue and sera of mice with cancer; potential biomarkers, specific for prostate and regulated in cancer tissue or serum; potential biomarkers specific for prostate and secreted; potential biomarkers highly regulated in prostate tissue or serum, preferably by a factor of more than four; potential biomarkers, prior knowledge-based selection, preferably characterised by known biological function during cancer progression; or a combination thereof, preferably a combination of at least five or most preferably of all of these criteria is used. Of these preferably specifically the following combination of criteria leads to biomarker systems which can finally be used for human diagnosis/therapy: biomarkers regulated in prostate tissue and serum; potential biomarkers regulated in prostate tissue and detected in serum; potential biomarkers regulated in prostate tissue and secreted; potential biomarkers highly regulated in prostate tissue or serum, preferably by a factor of more than four; potential biomarkers, prior knowledge-based selection, preferably characterised by known biological function during cancer progression.

Preferably selection takes place (selection meaning that the corresponding protein/fragment thereof (meaning protein or a fragment of such a protein) will enter the next step) if the factor between signals of healthy and signals of cancerous samples is either larger than 1.5 or smaller than 0.75. This in particular applies to the first three above-mentioned selection criteria.

Typically, in step (a) the proteins/peptides of the digested proteins of the samples are in a first step identified by using a (shotgun) mass spectrometric technique, and in a second step a combined liquid chromatography/mass spectrometry technique, preferably a label-free quantitation technique, is used for the identification of the differential properties (normally differential abundance) between healthy and cancerous samples. Preferably, within step (a) the mass spectrometrically detected proteins/protein fragment signals are attributed to the corresponding proteins by using database information attributing mass spectrometric signals to specific proteins/protein fragments.

According to a further preferred embodiment, in step (b) absolute quantification is achieved by using a quantitative internal standard, preferably a specifically synthesised internal standard.

It is further preferred to use in step (b) and/or in step (c) tandem mass spectrometry techniques, preferably selected reaction monitoring (SRM), preferably in combination with liquid chromatography, as mass spectrometry method. As concerns these techniques and their definitions and parameters, for keeping the present specification within reasonable boundaries, reference is made to the publication B. Domon and R. Aebersold, entitled Mass Spectrometry and Protein Analysis (Science 312, 121 (2006)) and the corresponding references cited therein. The disclosure of these documents is expressly included into this specification as concerns these analytical tools for the analysis of the proteome.

The present invention furthermore relates to a cancer diagnostic biomarker assay and/or therapeutic target which can be determined using a method as outlined above, or specifically determined using such a method. Specifically such a biomarker assay and/or therapeutic target may consist of the set as outlined further below in the context of the description of the corresponding methods, so for example a cancer diagnostic/therapeutic biomarker assay for localized prostate cancer can be based on, for the monitoring of localized prostate cancer, in particular for the distinction from benign prostate hyperplasia, a combined measurement of the concentration of at least two, preferably at least three proteins and/or fragments of proteins selected from the group derived from: ASPN; VTN; AOC3; LOX; PGCP; PSAP; THBS1; CFH; CLU; KIT; TFRC; LGALS3BP; GOLPH2; HYOU1; CTSD; OLFM4; AKAP13; CP; CPE; CPM; ICAM1; MSMB; TM9SF3; GALNTL4 in human serum, plasma or a derivative of blood, or blood itself. Gene names as given here, Entry names, Protein names (shortened) and Accession numbers as generally used in all this specification are as defined according to the UniProt Consortium, which is comprised of the European Bioinformatics Institute (EBI), the Swiss Institute of Bioinformatics (SIB), and the Protein Information Resource (PIR). Preferably the measurement is carried out using tandem mass spectrometry techniques, preferably selected reaction monitoring (SRM), more preferably in combination with liquid chromatography, and/or Enzyme-Linked Immunosorbent Assays (ELISA) for the detection of these proteins/fragments thereof.

The present invention furthermore relates to a cancer diagnostic biomarker assay and/or therapeutic target which can be determined using a method as outlined above, or specifically determined using such a method. Specifically such a biomarker assay and/or therapeutic target may consist of the set as outlined further below in the context of the description of the corresponding methods, so for example a cancer diagnostic/therapeutic biomarker assay for localized prostate cancer can be based on ASPN, and optionally VTN, in combination with one of AOC3; LOX; PGCP; PSAP; THBS1; CFH; CLU; KIT; TFRC; LGALS3BP; GOLPH2, HYOU1; CTSD; OLFM4 derived proteins/fragments thereof.

Furthermore the present invention relates to a cancer diagnostic/therapeutic biomarker assay for the diagnosis, therapy and/or the therapeutic monitoring of (human) diseases or dysfunctions, preferably of cancer, and most preferably of prostate cancer (localized or non-localized) comprising the measurement of at least two, preferably at least three or at least five protein/peptide biomarkers (as for example determined according to a method as given above) in human serum, plasma or any other derivatives of blood, or blood itself. The assay can for example be an antibody-based assay such as an Enzyme-Linked Immunosorbent Assay, it can however also be an LC-SRM assay.

To increase the reliability of such cancer diagnostic biomarker assay, it can be combined with an affinity reagent-based assay, e.g. an antibody-based assay such as Enzyme-Linked Immunosorbent Assay (ELISA) for the detection of further systems such as Prostate Specific Antigen (PSA). Also multiplexing techniques of a series of antibodies for example using bead techniques are possible in this respect.

The present invention furthermore relates to a method for the diagnosis of localized prostate cancer using a (preferably combined) measurement of the concentration of ASPN derived protein/fragments thereof as well as VTN derived protein/fragments thereof in human serum, plasma or any other derivatives of blood, or blood itself. For increasing the accuracy, it is preferred to carry out one (or even several) further measurements, namely the measurement of one further protein/fragments thereof selected from the group derived from: AOC3; LOX; PGCP; PSAP; THBS1. If combined with a PSA-measurement, the further protein/fragments thereof can additionally be selected from: CFH; CLU; KIT; TFRC; LGALS3BP; GOLPH2.

Preferably in such a method the measurement is carried out using tandem mass spectrometry techniques, preferably selected reaction monitoring (SRM), typically in combination with preceding liquid chromatography. Alternatively or additionally it is possible to use an antibody based assay such as an Enzyme-Linked Immunosorbent Assays (ELISA) for the detection of these proteins/fragments thereof. Combined approaches are possible, so for example one system (or group of systems) can be determined using SRM (if for example no ELISA is available), and the remaining system(s) can be determined by using antibody based techniques such as ELISA-techniques.

In such a method, typically for a positive diagnosis of localized prostate cancer
the concentration of ASPN derived protein/fragments thereof has to be more than 55 ng/ml, preferably more than 60 ng/ml, and optionally at the same time,
the concentration of VTN derived protein/fragments has to be less than 3500 ng/ml, preferably less than 3300 ng/ml.

If, as preferred, additionally one of the above-mentioned additional systems is measured,
the concentration of AOC3 derived protein/fragments thereof has to be less than 250 ng/ml, preferably less than 220 ng/ml, and/or the concentration of LOX derived protein/fragments thereof has to be less than 580 ng/ml, preferably less than 550 ng/ml,
and/or the concentration of PGCP derived protein/fragments thereof has to be more than 550 ng/ml, preferably more than 570 ng/ml,
and/or the concentration of PSAP derived protein/fragments thereof has to be less than 33000 ng/ml, preferably less than 32500 ng/ml, most preferably less than 32250 ng/ml,
and/or the concentration of THBS1 derived protein/fragments thereof has to be more than 12500 ng/ml, preferably more than 13000 ng/ml, most preferably more than 13500 ng/ml
and/or the concentration of LGALS3BP derived protein/fragments thereof has to be more than 390 ng/ml, preferably more than 400 ng/ml
and/or the concentration of GOLPH2 derived protein/fragments thereof has to be more than 80 ng/ml, preferably more than 90 ng/ml
and/or the concentration of HYOU1 derived protein/fragments thereof has to be more than 35 ng/ml, preferably more than 40 ng/ml,
and/or the concentration of CTSD derived protein/fragments thereof has to be less than 32 ng/ml, preferably less than 25 ng/ml,
and/or the concentration of OLFM4 derived protein/fragments thereof has to be less than 20 ng/ml, preferably less than 15 ng/ml.

Preferably in such a method the measurement is carried out for the diagnosis and/or for the therapy and/or for the monitoring of localized prostate cancer for the distinction from benign prostate hyperplasia, using a combined measurement of the concentration of at least three proteins and/or fragments of proteins selected from the group derived from: ASPN; HYOU1; CTSD; OLFM4; in human serum, plasma or a derivative of blood, or blood itself. For the diagnosis/monitoring preferably additionally the concentration of the Prostate Specific Antigen (PSA) in the human serum, plasma or a derivative of blood, or blood itself is measured using an affinity reagent-based, preferably an antibody-based assay such as an Enzyme-Linked Immunosorbent Assay (ELISA). Further preferably for a positive diagnosis the concentration of the Prostate Specific Antigen has to be more than 2 ng/ml, preferably more than 4 ng/ml.

In this context, preferably for a positive diagnosis or the monitoring of localized prostate cancer the concentration of ASPN derived protein/fragments thereof has to be more than 55 ng/ml, preferably more than 60 ng/ml; and/or the concentration of HYOU1 derived protein/fragments thereof has to be more than 35 ng/ml, preferably more than 40 ng/ml; and/or the concentration of CTSD derived protein/fragments thereof has to be less than 32 ng/ml, preferably less than 25 ng/ml; and/or the concentration of OLFM4 derived protein/fragments thereof has to be less than 20 ng/ml, preferably less than 15 ng/ml.

It should be noted in the context of the threshold concentrations as given above as well as a detailed further below that these may depend on the specific measurement technique, as for example the methods used here, namely SRM, will measure the total species, so e.g. free and bound species, while for example an antibody-based assay such as ELISA might be able to distinguish between these two forms leading to different threshold concentrations if the latter methods are used. The values given here therefore in particular relate to measurements using SRM-methods, and they might have to be adapted by analogy if different methods are being used. This is however a matter of conversion which is within the realm of the skills of the person skilled in the art in this field.

The present invention furthermore relates to an extremely high accuracy method for the diagnosis of metastatic prostate cancer using a (preferably combined) measurement of the concentration of ASPN and CTSD and THBS1 and GALNTL4 as well as VTN derived protein/fragments thereof in human serum, plasma or any other derivatives of blood, or blood itself, preferably in combination with the measurement of one further protein/fragments thereof selected from the group derived from: PSAP; GSPT1; CEACAM1; HYOU1; EFNA5; KIT.

Preferably, as in the above case of the methods for diagnosis of localized prostate cancer, the measurement is carried out using tandem mass spectrometry techniques, preferably selected reaction monitoring (SRM), more preferably in combination with liquid chromatography, and/or antibody based methods such as Enzyme-Linked Immunosorbent Assays (ELISA) for the detection of these proteins/fragments thereof.

For a positive diagnosis of non-localized (metastatic) prostate cancer
the concentration of ASPN derived protein/fragments thereof has to be more than 60 ng/ml, preferably more than 65 ng/ml, most preferably more than 68 ng/ml and at the same time
the concentration of CTSD derived protein/fragments has to be more than 120 ng/ml, preferably more than 130 ng/ml, most preferably more than 133 ng/ml and at the same time
the concentration of THBS1 derived protein/fragments has to be less than 12000 ng/ml, preferably less than 11500 ng/ml, most preferably less than 10750 ng/ml and at the same time the concentration of GALNTL4 derived protein/fragments has to be more than 1400 ng/ml, preferably more than 1600 ng/ml, most preferably more than 1650 ng/ml and at the same time
the concentration of VTN derived protein/fragments has to be more than 3000 ng/ml, preferably more than 3150 ng/ml, most preferably more than 3300 ng/ml.

If, as preferred, additionally one of the above-mentioned additional systems is measured,
the concentration of PSAP derived protein/fragments thereof has to be more than 33000 ng/ml, preferably more than 34000 ng/ml,
and/or the concentration of GSPT1 derived protein/fragments thereof has to be more than 450 ng/ml, preferably more than 500 ng/ml, more preferably more than 510 ng/ml,
and/or the concentration of CEACAM1 derived protein/fragments thereof has to be more than 35 ng/ml preferably more than 38 ng/ml, (this threshold value being the only one calculated in relation of ELISA determination)
and/or the concentration of HYOU1 derived protein/fragments thereof has to be more than 80 ng/ml, preferably more than 89 ng/ml,
and/or the concentration of EFNA5 derived protein/fragments thereof has to be more than 60 ng/ml, preferably more than 65 ng/ml,
and/or the concentration of KIT derived protein/fragments thereof has to be more than 90 ng/ml, preferably more than 95 ng/ml.

As mentioned above, it can be advantageous to combine the measurement of the above-mentioned systems, be it for localized or non-localized prostate cancer diagnosis, with the measurement of further parameters of the serum, plasma or any other derivatives of blood, or blood itself which are not the result of a biomarker determination method as outlined above. It is for example possible that for the diagnosis additionally the concentration of the Prostate Specific Antigen (PSA) in the human serum, plasma or any other derivatives of blood, or blood itself is measured using a corresponding antibody-based assay such as an Enzyme-Linked Immunosorbent Assay (ELISA), wherein for a positive diagnosis the concentration of the Prostate Specific Antigen (PSA) normally has to be more than 2 ng/ml, preferably more than 4 ng/ml.

Further embodiments of the present invention are outlined in the dependent claims.

SHORT DESCRIPTION OF THE FIGURES

Figure 2:
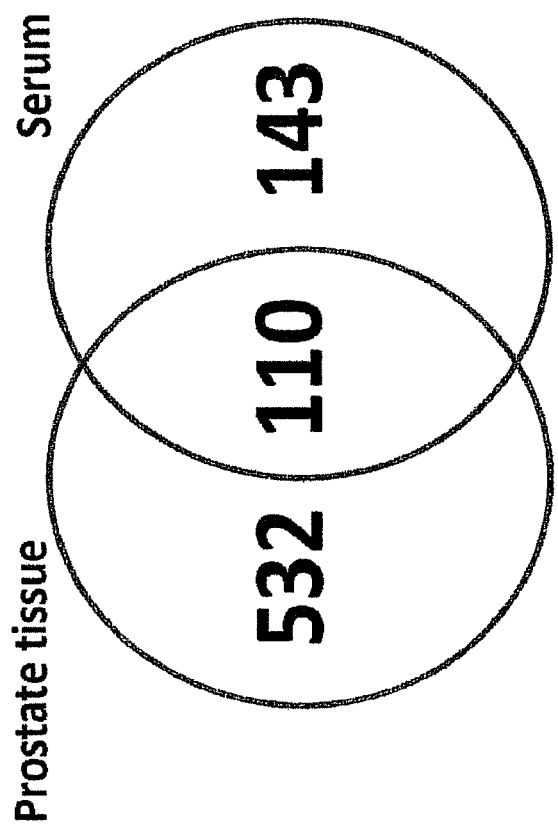

In the accompanying drawings preferred embodiments of the invention are shown in which:

FIG. 1 is an overview of the integrated proteomic approach for biomarker discovery, verification and validation. The scheme is divided in two main sections: First the discovery and verification phases performed using an animal model and second the validation phase with human patient samples; the numbers in italics indicate the number of glycoproteins that were identified and considered for the next step; wherein in a): selective enrichment of N-glycopeptides was performed from tissue and serum from healthy and cancerous mice to discover in vivo CaP-specific signatures using prostate tissue from a mouse model of CaP; this allows to create a catalogue of 785 glycoproteins which served as a resource for the later steps; MS-based label-free quantification was performed on the same murine tissue and serum samples; this resulted in a relative quantification of 352 glycoproteins comparing cancerous vs. benign samples; 164 glycoproteins matching criteria were then chosen for further investigation; wherein b): 41 of these biomarker candidates could be validated in sera of mice and wherein c): 43 candidates in human patients by MS based selected reaction monitoring (SRM) and ELISA; generally, the boundaries between the human and animal steps are flexible; e.g. it is possible to do the verification step also in human samples provided such a collection is actually available;

FIG. 2 shows an overview of the Mouse Glycoproteome Catalog, wherein the number of proteins identified in the mouse prostate tissue and serum are shown as a Venn diagram; the number of proteins that could be quantified is shown below; and FIG. 3 shows the discriminant accuracy of selected candidates in multivariate approaches; a patient is classified following a rule generated by the statistical software; the % of correct predictions is defined as accuracy of the model; as indicated above, Gene names are as defined according to the UniProt Consortium, which is comprised of the European Bioinformatics Institute (EBI), the Swiss Institute of Bioinformatics (SIB), and the Protein Information Resource (PIR); the shaded entries in the first lines indicate which systems can be interchanged within one assay.

DETAILED DESCRIPTION OF THE PREFERRED EMBODIMENTS

Referring to the drawings, which are for the purpose of illustrating the present preferred embodiments of the invention and not for the purpose of limiting the same, FIG. 1 shows an overview of the integrated proteomic approach for biomarker discovery, verification and validation. The scheme is divided in two main sections: First the discovery and verification phases (a) and (b) performed using an animal model (mice) and second the validation phase (c) with human patient samples.

In the following example the method is applied to the determination of biomarkers for prostate cancer. As outlined above, this shall however not be construed to the actual gist of the invention, as the method may equivalently be applied to other types of cancer such as breast cancer, lung cancer, ovarian cancer and the like and it may also equivalently be applied generally to other types of diseases or dysfunctions such as diabetes (mellitus and other types), neurodegenerative diseases: such as Alzheimer's disease, Parkinson's disease, Huntington's disease, Creutzfeldt-Jakob disease; autoimmune diseases: such as multiple sclerosis, rheumatoid arthritis; infectious diseases: such as malaria, HIV; cardiovascular disease: such as hypertension, atherosclerosis. As outlined above, the main strength of the animal model work is that specific, defined perturbations can be applied and that the consequences of these are being measured. The same perturbations can be also be relevant to other types of cancers, which means that it is possible to look at the markers as a rationale consequence of the induced perturbation as opposed to what the general term like disease related might suggest.

In the initial discovery phase, prostate tissue samples, serum samples and both on the one hand of healthy mice and of prostate cancerous mice were used, so four different series of experiments. For the determination of the differential behaviour only tissue samples of healthy/cancerous mice were compared, and on the other hand serum samples of healthy/cancerous mice were compared.

In a first step (a) the tissue (prepared as described in more detail below) and the serum samples were digested using trypsin, and from the corresponding proteome digests the N-linked glycosylated protein fragments were selected and extracted using the SPEG-technique (described in more detail below).

Subsequently glycoprotein identification was carried out using mass spectrometry, specifically a shotgun approach, without determining differential behaviour in this stage. This resulted in a total of 532 detected glycoproteins in prostate tissue and 253 detected glycoproteins in serum. A total of 785 glycoproteins were detected, as 110 proteins were detected in the tissue as well as in the serum (graphically illustrated in FIG. 2).

The next step designated with label-free quantitation aims at the detection of the differential behaviour of the signals of the protein fragments. The experiment is a combined liquid chromatography/mass spectrometry experiment in which mass spectrometry is carried out according to the elution profile of the chromatography. Using this experiment one can track the differential behaviour between healthy/cancerous samples. Those signals/protein fragments which in this label-free quantitation step did not show differential behaviour were rejected from the above-mentioned set of 785 glycoproteins, leading to 352 quantified proteins, of which 279 originate from the tissue samples and 160 from the serum samples (illustrated in FIG. 2).

These 352 quantified proteins are now further selected to only keep those which show a pronounced differential behaviour, and which comply with at least one of the eight rationales as given and discussed in the context of table 1 below. This after the filtering using the rationales leads to 164 potential candidate biomarker systems, which are resulting from the attribution of the signals to the specific glycoproteins by using electronic annotation.

In the second step (b), which is optional, verification or rather qualification using the nonhuman system takes place, wherein the final analytical tools which are to be used for the final biomarker assay method are used. In this step (b) correspondingly only serum of healthy/cancerous mice is analysed, it is again digested and the glycoproteins extracted as described in the context of (a), but subsequently selected reaction monitoring (SRM), i.e. a liquid chromatography/tandem mass spectrometry method is used for absolute quantitation of the systems using specifically provided (synthesised) internal standards for absolute quantitation.

Out of the 164 systems which have entered step (b) only 41 could be absolutely quantified mainly for practical reasons. The corresponding 41 systems are given in table 2 discussed in more detail below.

Therefore for the next step all the 164 systems having resulted from step (a) are used for the final step of validation (c). The results of step (b) are further verified by using RT-PCR, immunohistochemistry, western blot.

Within step (c) essentially the same procedure is carried out as within step (b) however this time using serum samples of human origin of healthy/cancerous individuals. From the SRM-side this leads to 37 candidates. Wherever possible, the 164 candidates having entered step (c) are furthermore validated using available ELISA assays, leading to an additional 11 possible candidates.

Due to the fact that certain systems result from the SRM verification as well as from the ELISA validation, this results in a final number of 43 candidate biomarker systems. These are listed in table 3.

From a principal point of view any of these, possibly in combination with one or several, can be used in an assay for the detection of prostate cancer.

In view of reducing the number of necessary measurements by at the same time keeping an as high as possible accuracy, statistical methods (for a more detailed discussion see further below) were applied to all 43 systems in correlation with the patient's data collection leading to the final assays as given in FIG. 3.

Five particularly high accuracy assays are given in FIG. 3 A), and one notes that in all of them ASPN as well as VTN are present. Correspondingly therefore glycoproteins derived from these genes or rather the fragments of these glycoproteins are highly indicative for the distinction between benign prostate hyperplasia (BPH) and localized prostatic cancer (locPCa). The corresponding accuracies are above 80%, so roughly around 20% higher than the accuracy of present state of the art PSA-methods.

Using additional incorporation of PSA-measurements using ELISA, one statistically finds further nine biomarker assays for discriminating between BPH and locPCa as given in FIG. 3 B). Again in all of these systems ASPN as well as VTN derived glycoproteins are present. The accuracies of these combined measurements are another 10% higher than without taking PSA-measurements into account, leading to a so far unreached exceedingly high accuracy for the detection of prostate cancer.

Using additional incorporation of PSA-measurements using ELISA and more data, one statistically finds further 5 biomarker assays for discriminating between BPH and locPCa as given in FIG. 3 C). In each of these systems three out of the systems of the group: ASPN, OLFM4, HYOU1, CTSD derived glycoproteins are present. The corresponding accuracies are again above 80%, so roughly around 20% higher than the accuracy of present state of the art PSA-methods.

Finally in FIG. 3 D) the statistical results for biomarker assays for the discrimination between locPCa and metCPa is given. Using the combined measurements of six systems in each assay one reaches 100% accuracy.

The above shows that the proposed method not only provides a powerful tool for targeted development of biomarker assays with high accuracy. It furthermore shows that for the specific situation of prostate cancer the correspondingly determined biomarker assays show an unexpectedly high accuracy which exceeds anything so far reported in the literature.

EXPERIMENTAL DETAILS (I) Translational approach: The translational approach is based on the initial identification of interesting candidate biomarkers in a mouse model for prostate cancer and the validation of such candidates in human clinical samples. To identify candidate biomarkers to be used in the clinics as defined diagnostic or therapeutical targets, we started to analyze the prostate tissue and blood from genetically defined mice that develop prostate cancer (Pten conditional knockout, cKO, see e.g. US 2006/0064768) and control mice that have intact Pten alleles and do not develop such tumors.

Rationales for using a mouse model: We decided to use the genetically defined Pten conditional knockout model because these mice develop early stage epithelial prostate cancers following deletion of the tumor suppressor gene Pten. The phenotype is closely related to human localized prostate cancer and is thus an ideal starting point for the identification of novel biomarkers that could distinguish human localized prostate cancer from benign hyperplastic lesions (Benign Prostatic Hyperplasia or BPH). Moreover, the use of a Pten cKO mouse model allows to identify therapeutical/imaging targets and biomarkers to be used specifically for stratified patients having PTEN mutations or any imbalance derived by mutations along the PTEN signaling pathway. The use of a mouse model facilitates the initial identification of candidate biomarkers since the prostate tissue is very homogeneous and major variables such as environmental conditions and timing can be controlled, in contrast to the highly heterogeneous human tissues. Interestingly, the ratio between prostate cancer tissue volume and total blood volume is 40-40000× higher in mice compared to men. This is of course an intrinsic advantage since variations in the blood proteome are expected to be better uncovered in such a model than in human patient samples. Finally only the murine tissue can be efficiently perfused in order to eliminate blood contaminations (see below). Blood protein contaminations in the tissues often mask the identification of proteins present at particular low concentration. Moreover, the absence of blood in the tissue following perfusion allows to apply comparative proteomics (blood-tissue) without any potential bias (see table 1, rationales 1, 2, 4, 7).

TABLE 1

Selection of interesting proteins for validation in human Sera

| | List of rationales: | Discriminant factor |
|---|---|---|
| 1 | potential biomarkers regulated in prostate tissue AND serum | >1.5 or <0.75 |
| 2 | potential biomarkers regulated in prostate tissue AND detected in serum | >1.5 or <0.75 |
| 3 | potential biomarkers regulated in prostate tissue AND secreted | >1.5 or <0.75 |
| 4 | potential biomarkers exclusively detected in prostate tissue AND sera of mice with cancer | |
| 5 | potential biomarkers, specific for prostate AND regulated in cancer tissue or serum | |
| 6 | potential biomarkers specific for prostate AND secreted | |
| 7 | potential biomarkers, top regulated in prostate tissue or serum (>4×) | |
| 8 | potential biomarkers, prior knowledge-based selection (biological function during cancer progression) | |

| | Rationale | Gene name | Entry name | Protein name | Accession number | annotated or predicted cellular localization (ref 6) |
|---|---|---|---|---|---|---|
| 1 | 1 | Ecm1 | ECM1_MOUSE | Extracellular matrix protein 1 | Q61508 | secreted |
| 2 | 1 | Egfr | EGFR_MOUSE | Epidermal growth factor receptor | Q01279 | plasma membrane/ secreted |
| 3 | 1 | Trf | TRFE_MOUSE | Serotransferrin | Q92111 | secreted |
| 4 | 1 | Pdia6 | PDIA6_MOUSE | Protein disulfide-isomerase A6 | Q922R8 | ER |
| 5 | 1 | Hsp90b1 | ENPL_MOUSE | Endoplasmin | P08113 | ER |
| 6 | 1 | Rnase1 | RNAS1_MOUSE | Ribonuclease pancreatic | P00683 | secreted |
| 7 | 1 | Lifr | LIFR_MOUSE | Leukemia inhibitory factor receptor | P42703 | plasma membrane |
| 8 | 2 | Ighg1 | IGH1M_MOUSE | Ig gamma-1 chain C region, membrane-bound form | P01869 | secreted |
| 9 | 2 | Clu | CLUS_MOUSE | Clusterin | Q06890 | secreted |
| 10 | 2 | Cfh | CFAH_MOUSE | Complement factor H | P06909 | secreted |
| 11 | 2 | H2-L | HA1L_MOUSE | H-2 class I histocompatibility antigen, L-D alpha chain | P01897 | plasma membrane |
| 12 | 2 | Col12a1 | COCA1_MOUSE | Collagen alpha-1(XII) chain | Q60847 | secreted |
| 13 | 2 | Dpp7 | DPP2_MOUSE | Dipeptidyl-peptidase 2 | Q9ET22 | lysosomal |
| 14 | 2 | Pgcp | O70216_MOUSE | Plasma glutamate carboxypeptidase | Q9WVJ3 | secreted? |
| 15 | 2 | Cp | CERU_MOUSE | Ceruloplasmin | Q61147 | secreted |
| 16 | 2 | Cfb | CFAB_MOUSE | Complement factor B | P04186 | secreted |
| 17 | 2 | Lrp1 | LRP1_MOUSE | Low-density lipoprotein receptor-related protein 1 | Q91ZX7 | secreted |
| 18 | 2 | Col1a1 | CO1A1_MOUSE | Collagen alpha-1(I) chain | P11087 | secreted |
| 19 | 2 | Itgav | ITAV_MOUSE | Integrin alpha-V | P43406 | plasma membrane |
| 20 | 2 | Lama3 | LAMA3_MOUSE | Laminin subunit alpha-3 | Q61789 | secreted |
| 21 | 2 | Fn1 | FINC_MOUSE | Fibronectin | P11276 | secreted |
| 22 | 2 | Anpep | AMPN_MOUSE | Aminopeptidase N | P97449 | plasma membrane |
| 23 | 2 | Ctse | CATE_MOUSE | Cathepsin E | P70269 | endosomal |
| 24 | 2 | Ctsa | PPGB_MOUSE | Lysosomal protective protein | P16675 | lysosomal |
| 25 | 2 | Ceacam1 | CEAM1_MOUSE | Carcinoembryonic antigen-related cell adhesion molecule 1 | P31809 | plasma membrane |
| 26 | 2 | Ace | ACET_MOUSE | Angiotensin-converting enzyme, testis-specific isoform | P22967 | plasma membrane/ secreted |
| 27 | 2 | Pdia3 | PDIA3_MOUSE | Protein disulfide-isomerase A3 | P27773 | ER |
| 28 | 2 | Sslp1 | SSLP1_MOUSE | Secreted seminal-vesicle Ly-6 protein 1 | Q3UN54 | secreted |
| 29 | 2 | Btd | BTD_MOUSE | Biotinidase | Q8CIF4 | secreted |
| 30 | 2 | Atp1b2 | AT1B2_MOUSE | Sodium/potassium-transporting ATPase subunit beta-2 | P14231 | plasma membrane |

TABLE 1-continued

Selection of interesting proteins for validation in human Sera

| | | | | | | |
|---|---|---|---|---|---|---|
| 31 | 2 | Hspa5 | GRP78_MOUSE | 78 kDa glucose-regulated protein | P20029 | ER |
| 32 | 2 | Psap | SAP_MOUSE | Sulfated glycoprotein 1 | Q61207 | secreted |
| 33 | 2 | Thbs1 | TSP1_MOUSE | Thrombospondin 1 | P35441 | secreted |
| 34 | 2 | Adcy3 | ADCY3_MOUSE | Adenylate cyclase type 3 | Q8VHH7 | plasma membrane |
| 35 | 2 | Ctbs | DIAC_MOUSE | Di-N-acetylchitobiase | Q8R242 | lysosomal |
| 36 | 2 | Ggh | GGH_MOUSE | Gamma-glutamyl hydrolase | Q9Z0L8 | secreted/lysosomal |
| 37 | 2 | Serping1 | IC1_MOUSE | Plasma protease C1 inhibitor | P97290 | secreted/plasma? |
| 38 | 2 | L1cam | L1CAM_MOUSE | Neural cell adhesion molecule L1 | P11627 | plasma membrane |
| 39 | 2 | 1100001H23Rik | PLBL1_MOUSE | Putative phospholipase B-like 1 | Q8VCI0 | secreted |
| 40 | 2 | Qsox1 | QSOX1_MOUSE | Sulfhydryl oxidase 1 | Q8BND5 | secreted/Golgi membrane |
| 41 | 2 | Lrg1 | Q91XL1_MOUSE | Leucine-rich alpha-2-glycoprotein | Q91XL1 | secreted/plasma? |
| 42 | 2 | Lgals3bp | O35649_MOUSE | Cyclophilin C-associated protein | O35649 | plasma membrane |
| 43 | 2 | Cd44 | CD44_MOUSE | CD44 antigen | P15379 | plasma membrane |
| 44 | 3 | Col14a1 | COEA1_MOUSE | Collagen alpha-1(XIV) chain | Q80X19 | secreted |
| 45 | 3 | Fam3d | FAM3D_MOUSE | Protein FAM3D | P97805 | secreted |
| 46 | 3 | Pon3 | PON3_MOUSE | Serum paraoxonase/lactonase 3 | Q62087 | secreted |
| 47 | 3 | Timp1 | TIMP1_MOUSE | Metalloproteinase inhibitor 1 | P12032 | secreted |
| 48 | 3 | Abca16 | Q6XBG1_MOUSE | ATP-binding cassette transporter sub-family A member 16 | Q6XBG1 | plasma? Membrane/secreted? |
| 49 | 3 | Fbn1 | FBN1_MOUSE | Fibrillin-1 | Q61554 | secreted |
| 50 | 3 | Lum | LUM_MOUSE | Lumican | P51885 | secreted |
| 51 | 3 | Lamb2 | LAMB2_MOUSE | Laminin subunit beta-2 | Q61292 | secreted |
| 52 | 3 | Vcan | CSPG2_MOUSE | Versican core protein | Q62059 | secreted |
| 53 | 3 | Bgn | PGS1_MOUSE | Biglycan | P28653 | secreted |
| 54 | 3 | Enpp5 | ENPP5_MOUSE | Ectonucleotide pyrophosphatase/phosphodiesterase family member 5 | Q9EQG7 | secreted |
| 55 | 3 | Erap1 | ERAP1_MOUSE | Endoplasmatic reticulum aminopeptidase 1 | Q9EQH2 | secreted |
| 56 | 3 | Pxdn | PXDN_MOUSE | Peroxidasin homolog | Q3UQ28 | secreted/ER |
| 57 | 3 | Col6a3 | O88493_MOUSE | Type VI collagen alpha 3 subunit | O88493 | secreted |
| 58 | 3 | Emilin1 | EMIL1_MOUSE | EMILIN-1 | Q99K41 | secreted |
| 59 | 3 | Mfap4 | MFAP4_MOUSE | Microfibril-associated glycoprotein 4 | Q9D1H9 | secreted |
| 60 | 3 | Agrn | O08860_MOUSE | Agrin | O08860 | secreted |
| 61 | 3 | Prelp | PRELP_MOUSE | Prolargin | Q9JK53 | secreted |
| 62 | 3 | Lamc1 | LAMC1_MOUSE | Laminin subunit gamma-1 | P02468 | secreted |
| 63 | 3 | Lama1 | LAMA1_MOUSE | Laminin subunit alpha-1 | P19137 | secreted |
| 64 | 3 | Lama5 | LAMA5_MOUSE | Laminin subunit alpha-5 | Q61001 | secreted |
| 65 | 3 | Lama2 | LAMA2_MOUSE | Laminin subunit alpha-2 | Q60675 | secreted |
| 66 | 3 | Col6a5 | A6H586_MOUSE | Collagen type VI alpha 5 | A6H586 | secreted |
| 67 | 3 | Lamb1-1 | LAMB1_MOUSE | Laminin subunit beta-1 | P02469 | secreted |
| 68 | 3 | Creg1 | CREG1_MOUSE | Protein CREG1 | O88668 | secreted |
| 69 | 3 | Sva | Q64367_MOUSE | Seminal vesicle autoantigen | Q64367 | secreted |
| 70 | 3 | Serpinb6 | SPB6_MOUSE | Serpin B6 | Q60854 | plasma membrane?/secreted? |
| 71 | 3 | Cpe | CBPE_MOUSE | Carboxypeptidase E | Q00493 | secretory granules |
| 72 | 3 | 9530002K18Rik | SPIKL_MOUSE | Serine protease inhibitor kazal-like protein | Q8CEK3 | secreted |
| 73 | 3 | Olfm4 | OLFM4_MOUSE | Olfactomedin-4 | Q3UZZ4 | secreted |
| 74 | 3 | Lama4 | LAMA4_MOUSE | Laminin subunit alpha-4 | P97927 | secreted |
| 75 | 3 | Fcgbp | A1L0S2_MOUSE | LOC100037259 protein | A1L0S2 | secreted/ER?/golgi? |
| 76 | 3 | Dmbt1 | DMBT1_MOUSE | Deleted in malignant brain tumors 1 protein | Q60997 | secreted/plasma membrane |
| 77 | 3 | Wfdc3 | Q14AE4_MOUSE | Wap four-disulfide core domain 3 | Q14AE4 | secreted |
| 78 | 3 | Spink5 | Q5K5D4_MOUSE | Spink5 protein | Q5K5D4 | secreted |
| 79 | 3 | Ngp | Q61903_MOUSE | Myeloid secondary granule protein | Q61903 | secreted |
| 80 | 3 | Col7a1 | CO7A1_MOUSE | Collagen alpha-1(VII) chain | Q63870 | secreted |
| 81 | 3 | Itih5 | ITIH5_MOUSE | Inter-alpha-trypsin inhibitor heavy chain H5 | Q8BJD1 | secreted |
| 82 | 3 | Hyal6 | Q8CDQ9_MOUSE | Hypothetical Glycoside hydrolase family 56 containing protein | Q8CDQ9 | secreted? |
| 83 | 3 | BC023744 | Q0P6B3_MOUSE | BC023744 protein | Q0P6B3 | secreted |
| 84 | 3 | Aspn | ASPN_MOUSE | Asporin | Q99MQ4 | secreted |
| 85 | 4 | Postn | POSTN_MOUSE | Periostin | Q62009 | secreted |

TABLE 1-continued

Selection of interesting proteins for validation in human Sera

| | | | | | | |
|---|---|---|---|---|---|---|
| 86 | 4 | Fmr1 | FMR1_MOUSE | Fragile X mental retardation protein 1 homolog | P35922 | secreted?/cytoplasmic |
| 87 | 4 | Golga5 | GOGA5_MOUSE | Golgin subfamily A member 5 | Q9QYE6 | Golgi |
| 88 | 4 | Grn | GRN_MOUSE | Granulins | P28798 | secreted |
| 89 | 4 | Man2b1 | MA2B1_MOUSE | Lysosomal alpha-mannosidase | O09159 | lysosomal |
| 90 | 4 | Nav1 | NAV1_MOUSE | Neuron navigator 1 | Q8CH77 | cytoplasmic |
| 91 | 4 | Ramp3 | RAMP3_MOUSE | Receptor activity-modifying protein 3 | Q9WUP1 | plasma membrane |
| 92 | 5 | Tspan1 | Q99J59_MOUSE | Tetraspanin 1 | Q99J59 | plasma membrane |
| 93 | 5 | 5430419D17Rik | Q8BZE1_MOUSE | hypothetical Speract receptor | Q8BZE1 | plasma membrane |
| 94 | 5 | Grk5 | GRK5_MOUSE | G protein-coupled receptor kinase 5 | Q8VEB1 | cytoplasmic |
| 95 | 5 | Azgp1 | ZA2G_MOUSE | Zinc-alpha-2-glycoprotein | Q64726 | secreted |
| 96 | 6 | Spink3 | ISK3_MOUSE | Serine protease inhibitor Kazal-type 3 | P09036 | secreted |
| 97 | 6 | Egf | EGF_MOUSE | Pro-epidermal growth factor | P01132 | plasma membrane/secreted |
| 98 | 6 | Msmb | MSMB_MOUSE | Beta-microseminoprotein | O08540 | secreted |
| 99 | 6 | Creld2 | CREL2_MOUSE | Cysteine-rich with EGF-like domain protein 2 | Q9CYA0 | secreted/ER |
| 100 | 6 | Pbsn | PBAS_MOUSE | Probasin | O08976 | secreted |
| 101 | 6 | Sbp | SPBP_MOUSE | Prostatic spermine-binding protein | P15501 | secreted |
| 102 | 7 | Ermp1 | ERMP1_MOUSE | Endoplasmatic reticulum metallopeptidase 1 | Q3UVK0 | ER membrane |
| 103 | 7 | Pigr | PIGR_MOUSE | Polymeric-immunoglobulin receptor | O70570 | plasma membrane |
| 104 | 7 | Cadm1 | CADM1_MOUSE | Cell adhesion molecule 1 | Q8R5M8 | plasma membrane |
| 105 | 7 | Golph2 | GOLM1_MOUSE | Golgi phosphoprotein 2 | Q91XA2 | Golgi |
| 106 | 7 | Tspan8 | Q8R3G9_MOUSE | Tspan8 | Q8R3G9 | plasma membrane |
| 107 | 7 | Adam3 | Q62287_MOUSE | Cyritestin | Q62287 | plasma membrane |
| 108 | 7 | Thy1 | THY1_MOUSE | Thy-1 membrane glycoprotein | P01831 | plasma membrane |
| 109 | 7 | Mme | NEP_MOUSE | Neprilysin | Q61391 | plasma membrane |
| 110 | 7 | Apmap | APMAP_MOUSE | Adipocyte plasma membrane-associated protein | Q9D7N9 | plasma membrane |
| 111 | 7 | Ergic3 | ERGI3_MOUSE | Endoplasmatic reticulum-Golgi intermediate compartment protein 3 | Q9CQE7 | ER/Golgi |
| 112 | 7 | 9530003J23Rik | Q8BM27_MOUSE | Weakly similar to LYSOZYME C, TYPE M | Q8BM27 | secreted |
| 113 | 7 | Ceacam10 | CEAMA_MOUSE | Carcinoembryonic antigen-related cell adhesion molecule 10 | Q61400 | secreted |
| 114 | 7 | Plxna3 | P70208_MOUSE | Plexin 3 | P70208 | plasma membrane |
| 115 | 7 | Vmn2r10 | O35204_MOUSE | Putative pheromone receptor | O35204 | plasma membrane |
| 116 | 7 | Hyou1 | HYOU1_MOUSE | Hypoxia up-regulated protein 1 | Q9JKR6 | secreted/ER |
| 117 | 7 | Defb50 | BD50_MOUSE | Beta-defensin 50 | Q6TU36 | secreted |
| 118 | 7 | Fcgbp | Q8BZG2_MOUSE | hypothetical von Willebrand factor type D protein | Q8BZG2 | secreted |
| 119 | 7 | Rai2 | RAI2_MOUSE | Retinoic acid-induced protein 2 | Q9QVY8 | nuclear |
| 120 | 7 | Pnliprp1 | LIPR1_MOUSE | Pancreatic lipase-related protein 1 | Q5BKQ4 | secreted |
| 121 | 7 | Pdia2 | Q14AV9_MOUSE | Pdia2 protein | Q14AV9 | ER membrane |
| 122 | 7 | Hp | HPT_MOUSE | Haptoglobin | Q61646 | secreted/plasma |
| 123 | 7 | Cpm | CBPM_MOUSE | Carboxypeptidase M | Q80V42 | plasma membrane |
| 124 | 7 | Pigs | PIGS_MOUSE | GPI transamidase component PIG-S | Q6PD26 | ER |
| 125 | 7 | Mup3 | MUP3_MOUSE | Major urinary protein 3 | P04939 | secreted |
| 126 | 7 | Gc | VTDB_MOUSE | Vitamin D-binding protein | P21614 | secreted |
| 127 | 7 | Prom1 | PROM1_MOUSE | Prominin-1 | O54990 | plasma membrane |
| 128 | 7 | Vtn | VTNC_MOUSE | Vitronectin | P29788 | secreted |
| 129 | 7 | Aoc3 | AOC3_MOUSE | Membrane copper amine oxidase | O70423 | plasma membrane |
| 130 | 8 | Lamp1 | LAMP1_MOUSE | Lysosome-associated membrane glycoprotein 1 | P11438 | lysosomal |
| 131 | 8 | Lamp2 | LAMP2_MOUSE | Lysosome-associated membrane glycoprotein 2 | P17047 | lysosomal |
| 132 | 8 | Itgb1 | ITB1_MOUSE | Integrin beta-1 | P09055 | plasma membrane |
| 133 | 8 | Itgae | ITAE_MOUSE | Integrin alpha-E | Q60677 | plasma membrane |
| 134 | 8 | Flt4 | VGFR3_MOUSE | Vascular endothelial growth factor receptor 3 | P35917 | plasma membrane |
| 135 | 8 | Tnc | TENA_MOUSE | Tenascin | Q80YX1 | secreted |
| 136 | 8 | Fap | SEPR_MOUSE | Seprase | P97321 | secreted |

TABLE 1-continued

Selection of interesting proteins for validation in human Sera

| | | | | | | |
|---|---|---|---|---|---|---|
| 137 | 8 | Asph | Q6P8S1_MOUSE | Aspartate-beta-hydroxylase | Q6P8S1 | ER |
| 138 | 8 | Asah1 | ASAH1_MOUSE | Acid ceramidase | Q9WV54 | lysosomal |
| 139 | 8 | Atrn | ATRN_MOUSE | Attractin | Q9WU60 | plasma membrane |
| 140 | 8 | Cacna2d1 | CA2D1_MOUSE | Voltage-dependent calcium channel subunit alpha-2/delta-1 | O08532 | plasma membrane |
| 141 | 8 | Chl1 | CHL1_MOUSE | Neural cell adhesion molecule L1 | P70232 | plasma membrane/secreted |
| 142 | 8 | Ctsd | CATD_MOUSE | Cathepsin D | P18242 | lysosomal |
| 143 | 8 | Dpp4 | DPP4_MOUSE | Dipeptidyl peptidase 4 | P28843 | plasma membrane/secreted |
| 144 | 8 | Gba | GLCM_MOUSE | Glucosylceramidase | P17439 | lysosomal |
| 145 | 8 | Ncam1 | NCA12_MOUSE | Neural cell adhesion molecule 1 | P13594 | plasma membrane |
| 146 | 8 | Plxnb2 | Q3UH76_MOUSE | Plexin B2 | Q3UH76 | plasma membrane |
| 147 | 8 | Ptprj | PTPRJ_MOUSE | Protein-type tyrosine-protein phosphatase eta | Q64455 | plasma membrane |
| 148 | 8 | Ptprk | PTPRK_MOUSE | Receptor-type tyrosine-protein phosphatase kappa | P35822 | plasma membrane |
| 149 | 8 | Sirpa | SHPS1_MOUSE | Tyrosine-protein phosphatase non-receptor type substrate 1 | P97797 | plasma membrane |
| 150 | 8 | Kit | KIT_MOUSE | Mast/stem cell growth factor receptor | P05532 | plasma membrane |
| 151 | 8 | Sema4d | SEM4D_MOUSE | Semaphorin-4D | O09126 | plasma membrane |
| 152 | 8 | Apob48r | AB48R_MOUSE | Apolipoprotein B-100 receptor | Q8VBT6 | plasma membrane |
| 153 | 8 | Agtr1 | AGTRA_MOUSE | Type-1A angiotensin II receptor | P29754 | plasma membrane |
| 154 | 8 | Tm9sf3 | TM9S3_MOUSE | Transmembrane 9 superfamily member 3 | Q9ET30 | plasma membrane? |
| 155 | 8 | Galntl4 | GLTL4_MOUSE | Polypeptide n-acetylgalactosaminyl-transferase | Q8K1B9 | Golgi |
| 156 | 8 | Efna5 | EFNA5_MOUSE | Ephrin-a5 | O08543 | plasma membrane |
| 157 | 8 | F5 | O88783_MOUSE | Coagulation factor V | O88783 | secreted |
| 158 | 8 | Nptn | NPTN_MOUSE | Neuroplastin | P97300 | plasma membrane |
| 159 | 8 | Lox | LYOX_MOUSE | Protein-lysine 6-oxidase | P28301 | secreted |
| 160 | 8 | Mmel1 | MMEL1_MOUSE | Membrane metallo-endopeptidase-like 1 | Q9JLI3 | plasma membrane |
| 161 | 8 | Tfrc | TFR1_MOUSE | Transferrin receptor | Q62351 | plasma membrane |
| 162 | 8 | Gspt1 | Q8K2E1_MOUSE | G1 to S phase transition 1 | Q8K2E1 | |
| 163 | 8 | Akap13 | Q3T998_MOUSE | A kinase (PRKA) anchor protein 13 | Q3T998 | |
| 164 | 8 | Vasn | VASN_MOUSE | Vasorin | Q9CZT5 | plasma membrane |
| 165 | 8 | Icam1 | ICAM1_MOUSE | Intercellular adhesion molecule 1 | P13597 | plasma membrane |

Table 1: Selection of interesting proteins for validation in human sera. 165 glycoproteins detected in the mouse serum and tissue were selected for verification through targeted mass spectrometry and later validation in human clinical samples. Gene names, Entry names, Protein names (shortened) and Accession numbers as generally used in this specification are as defined according to the UniProt Consortium, which is comprised of the European Bioinformatics Institute (EBI), the Swiss Institute of Bioinformatics (SIB), and the Protein Information Resource (PIR). The annotated or predicted cellular localization is according to Emanuelsson O, Brunak S, von Heijne G, Nielsen H. (2007) Locating proteins in the cell using TargetP, SignalP and related tools. Nat Protoc. 2, 953-71.

Rationales for using mice and not cell culture systems: Proteomics techniques are easily applied to cell lines in vitro, whereas the use of in vivo models requires more complex handling and initial trouble-shootings. We decided to use an in vivo model however, because this mimics more closely the complexity of the human disease compared to in vitro models. The approach presented here is thus unique as very few screens today are applied to freshly isolated organs.

Tissue and blood extraction procedure: Mice are anesthetized and blood is extracted by pinning the left heart ventricle. Mice are subsequently heart perfused. This allows for the complete removal of blood from the prostate tissue. Tissue samples are then dissected and pure prostate tissue is readily snap-frozen and pulverized by using a mortar and pestle in the presence of liquid nitrogen. Serum is extracted from the blood and stored at −80° C. until use.

(II) Cutting edge mass-spectrometry (MS) and bioinformatics: Rationales for focusing on the N-linked glycoproteome: In order to find candidate biomarkers, we decided to focus on a particular and highly relevant subproteome, the N-linked glycosylated proteins. Protein glycosylation has long been recognized as a common post-translational modification. Typically, glycans are linked to serine or threonine residues (O-linked glycosylation) or to asparagine residues (N-linked glycosylation). N-linked glycosylation sites generally fall into the N×S/T sequence motif in which x denotes any amino acid except proline. The glycosylation of proteins is a characteristic post-translational modification of proteins residing in the extracellular space. This means that the vast majority of proteins that are specifically secreted or shed by the tumor and released into the bloodstream (which makes them highly valuable biomarker candidates) are glycosylated. Moreover, the enrichment of glycoproteins enables to unmask interesting candidates present at particular low concentration because highly abundant, non-glycosylated and non-relevant proteins such as cytoskeletal proteins in tissue samples as well as albumin (present at 35-50 mg/ml) in the serum samples are excluded from the measurements.

N-linked glycopeptide extraction procedure and quantification: To identify N-linked glycoproteins, we employed a method for the solid phase extraction of N-glycopeptides (SPEG) from tissue and serum according to Zhang, H., Li, X. J., Martin, D. B., and Aebersold, R. (2003) Identification and quantification of N-linked glycoproteins using hydrazide chemistry, stable isotope labeling and mass spectrometry; Nat Biotechnol 21, 660-666, the disclosure of which is expressly included into the specification as concerns SPEG. Glycopeptides are coupled to a solid support via their glycan moieties. Non-glycosylated peptides are then washed away and N-glycopeptides can be specifically released using the enzyme PNGase F. The method can be applied to tissue and serum alike.

The high mass accuracy and retention time reproducibility of the mass spectrometer instrument setup used (LTQ-FT instrument), in combination with the trans proteomic pipeline (TPP) software suite and SuperHirn (see e.g. Mueller et al. An Assessment of Software Solutions for the Analysis of Mass Spectrometry Based Quantitative Proteomics Data. J Proteome Res (2008) vol. 7 (1) pp. 51-61), allowed for the identification and direct label-free quantification of common peptide features. Thereby, peptide elution profiles from different runs were compared and glycoprotein ratios were calculated from the N-glycopeptides belonging to the same protein. Verification and validation phase: In order to verify our findings from the initial discovery phase, a list of interesting proteins selected by various rationales were quantified in the corresponding murine sera by targeted mass spectrometry via selected reaction monitoring (SRM, see e.g. Stahl-Zeng, J., Lange, V., Ossola, R., Eckhardt, K., Krek, W., Aebersold, R., and Domon, B. (2007) High sensitivity detection of plasma proteins by multiple reaction monitoring of N-glycosites. Mol Cell Proteomics 6, 1809-1817.).

This novel approach allows the simultaneous detection and quantification of proteins comparable in sensitivity to classical immunodetection procedures (e.g. Enzyme-Linked ImmunoSorbent Assay, ELISA), but with the advantage of not requiring tedious optimization steps for each biomarker candidate and generation of new antibodies. The SRM experiment is accomplished by specifying the parent mass of the compound for MS/MS fragmentation and then specifically monitoring for a single fragment ion. Thus, SRM delivers a unique fragment ion that can be monitored and quantified in the midst of a very complicated matrix. Stable isotope labeled peptides corresponding to the targeted N-glycosites (A peptide that was N-glycosylated in the intact protein in its de-glycosylated form) were synthesized and used as internal standards. This allowed for the absolute quantification of endogenous glycoproteins present in the mice sera (Table 2).

TABLE 2

Glycoproteins measured by SRM in murine sera

|    | Gene name | Protein name | Accession number | p-value 8 weeks | p-value 18 weeks |
|----|-----------|--------------|------------------|-----------------|------------------|
| 1  | Anpep     | Aminopeptidase N | P97449 | 0.4524 | 0.8517 |
| 2  | Asah1     | Acid ceramidase | Q9WV54 | 0.6247 | 0.0186 |
| 3  | Aspn      | Asporin | Q99MQ4 | 0.2619 | 0.0068 |
| 4  | Atp1b2    | Sodium/potassium-transporting ATPase subunit beta-2 | P14231 | 0.6055 | 0.0894 |
| 5  | Atrn      | Attractin | Q9WU60 | 0.7464 | 0.0079 |
| 6  | Cacna2d1  | Voltage-dependent calcium channel subunit alpha-2/delta-1 | O08532 | 0.6186 | 0.1576 |
| 7  | Cadm1     | Cell adhesion molecule 1 | Q8R5M8 | 0.8260 | 0.0670 |
| 8  | Chl1      | Neural cell adhesion molecule 1 | P70232 | 0.9771 | 0.0258 |
| 9  | Clu       | Clusterin | Q06890 | 0.7098 | 0.1500 |
| 10 | Cpm       | Carboxypeptidase M | Q80V42 | 0.3680 | 0.1460 |
| 11 | Ctsd      | Cathepsin D | P18242 | 0.5680 | 0.0176 |
| 12 | Dpp4      | Dipeptidyl peptidase 4 | P28843 | 0.2811 | 0.1521 |
| 13 | Ecm1      | Extracellular matrix protein 1 | Q61508 | 0.9629 | 0.0322 |
| 14 | Fap       | Seprase | P97321 | 0.6198 | 0.1000 |
| 15 | Flt4      | Vascular endothelial growth factor receptor 3 | P35917 | 0.9818 | 0.1180 |
| 16 | Fn1       | Fibronectin | P11276 | 0.7536 | 0.2586 |
| 17 | Gba       | Glucosylceramidase | P17439 | 0.2033 | 0.0070 |
| 18 | Golph2    | Golgi phosphoprotein 2 | Q91XA2 | 0.2742 | 0.0114 |
| 19 | Hyou1     | Hypoxia up-regulated protein 1 | Q9JKR6 | 0.4711 | 0.0352 |
| 20 | L1cam     | Neural cell adhesion molecule L1 | P11627 | 0.5814 | 0.7871 |
| 21 | Lamp1     | Lysosome-associated membrane glycoprotein 1 | P11438 | 0.7962 | 0.0939 |
| 22 | Lamp2     | Lysosome-associated membrane glycoprotein 2 | P17047 | 0.0206 | 0.0504 |
| 23 | Lgals3bp  | Cyclophilin C-associated protein | O35649 | 0.4300 | 0.0800 |
| 24 | Lifr      | Leukemia inhibitory factor receptor | P42703 | 0.3391 | 0.0066 |
| 25 | Lrp1      | Low-density lipoprotein receptor-related protein 1 | Q91ZX7 | 0.6288 | 0.0336 |
| 26 | Ncam1     | Neural cell adhesion molecule 1 | P13594 | 0.7807 | 0.0412 |
| 27 | Nptn      | Neuroplastin | P97300 | 0.3157 | 0.7977 |
| 28 | Pgcp      | Plasma glutamate carboxypeptidase | Q9WVJ3 | 0.8894 | 0.0635 |
| 29 | Pigr      | Polymeric-immunoglobulin receptor | O70570 | 0.4333 | 0.3961 |
| 30 | Plxnb2    | Plexin B2 | Q3UH76 | 0.4965 | 0.0243 |
| 31 | Pnliprp1  | Pancreatic lipase-related protein 1 | Q5BKQ4 | 0.9855 | 0.0194 |
| 32 | Postn     | Periostin | Q62009 | 0.2395 | 0.0954 |
| 33 | Prom1     | Prominin-1 | O54990 | 0.8580 | 0.3555 |
| 34 | Psap      | Sulfated glycoprotein 1 | Q61207 | 0.6845 | 0.1519 |
| 35 | Ptprj     | Receptor-type tyrosine-protein phosphatase eta | Q64455 | 0.7613 | 0.1003 |
| 36 | Ptprk     | Receptor-type tyrosine-protein phosphatase kappa | P35822 | 0.6358 | 0.0095 |
| 37 | Sirpa     | Tyrosine-protein phosphatase non-receptor type substrate 1 | P97797 | 0.7780 | 0.1677 |
| 38 | Thbs1     | Thrombospondin 1 | P35441 | NA | 0.0110 |
| 39 | Tnc       | Tenascin | Q80YX1 | 0.9564 | 0.1920 |

TABLE 2-continued

Glycoproteins measured by SRM in murine sera

|    | Gene name | Protein name | Accession number | p-value 8 weeks | p-value 18 weeks |
|----|-----------|--------------|------------------|-----------------|------------------|
| 40 | Vasn      | Vasorin      | Q9CZT5           | 0.4737          | 0.1717           |
| 41 | Vtn       | Vitronectin  | P29788           | 0.3433          | 0.2021           |

Table 2: List of 41 serum glycoproteins measured by SRM in murine sera from controls and mice with prostate cancer at 8 and 18 weeks of age. p-values below 0.05 indicate a statistical significant difference between the normal mice (n = 3) and mice with prostate cancer (n = 3) for the corresponding protein.
Experiments were performed on 8 and 18-week old mice. Gene name, Protein name (shortened) and Accession number are defined as given in Table 1.

Highly sensitive and selective analyses were performed by monitoring fragmentation channels specific to each peptide of interest in the sera of control mice (healthy) and mice with prostate cancer (cancerous). The human orthologues of the potential biomarkers detected in mouse were then validated in human sera using standard ELISA techniques and again targeted mass spectrometry.

(III) Multivariate statistical methods: Rationales and advantages on using multivariate methods: Signatures or combination of biomarker detection can lead to increased diagnostic accuracy, when compared with the use of single biomarker detection. This is the case when total and free PSA are used at the same time to diagnose prostate cancer. In our case, we have measured a panel of candidate biomarkers and we can now ask what signatures can best discriminate between BPH and localized prostate cancer (locPCa) or between localized and non-localized, i.e. metastatic prostate cancer (metPCa). Moreover we can find out what are the biomarkers commonly shared in all signatures, making them highly valuable in terms of intellectual property. In order to classify patients based on a biomarker signature, we performed quadratic discriminance analysis. The goal of the discriminance analysis is to determine a rule by which an individual is allocated to one of 2 or more groups (e.g. BPH and locPCa), based on the independent variables (biomarkers) that are measured in such an individual. The parameters that describe this rule are computed from the analysis of variables of all individuals with already known classification. In order to estimate the bias of the discriminant rule, we apply Jacknife leave one-out cross validation. Analyses were performed using the statistical software packages SYSTAT 12 and SPSS14.0.

Results:

Initially, we extracted N-glycopeptides from the perfused prostate tissue and serum of both control and cancer-bearing mice. We identified in total 642 glycoproteins from prostate tissue and 253 glycoproteins from serum. 110 proteins were commonly detected. We could thus generate a catalog comprising of 785 N-glycoproteins in total. From the initial mouse glycoprotein catalog, we could quantify 279 glycoproteins from tissue and 160 glycoproteins from serum comparing samples from mice with cancer and their respective controls (FIG. 2). Out of these proteins, 165 glycoproteins fulfilling at least one of the rationales listed in Table 1 were found to be potential biomarkers and therefore chosen for further verification.

Using SRM on the murine serum samples, we could verify and quantify 41 out of the 165 initial candidates. (Table 2)

46 candidate biomarkers which were either already tested in mice sera via SRM or promising candidates that showed up in the initial discovery phase from murine prostate tissue (Table 3) were further validated on 52 human serum samples. This was done by applying ELISA and SRM.

TABLE 3

List of 43 serum glycoproteins measured in human sera

|    | Gene name | Protein name | Accession number | Technique used for analysis |
|----|-----------|--------------|------------------|------------------------------|
| 1  | AGTR1     | Type-1 angiotensin II receptor | P30556 | SRM |
| 2  | AKAP13    | A-kinase anchor protein 13 | Q12802 | SRM |
| 3  | AOC3      | Membrane copper amine oxidase | Q16853 | SRM |
| 4  | APOB      | Apolipoprotein B-100 | P04114 | SRM |
| 5  | ASPN      | Asporin | Q9BXN1 | SRM |
| 6  | ATRN      | Attractin | O75882 | SRM |
| 7  | AZGP1     | Zinc-alpha-2-glycoprotein | P25311 | SRM |
| 8  | CADM1     | Cell adhesion molecule 1 | Q9BY67 | SRM |
| 9  | CEACAM1   | Carcinoembryonic antigen-related cell adhesion molecule 1 | P13688 | ELISA, SRM |
| 10 | CFH       | Complement factor H | P08603 | SRM |
| 11 | CLU       | Clusterin precursor | P10909 | SRM |
| 12 | CP        | Ceruloplasmin | P00450 | SRM |
| 13 | CPM       | Carboxypeptidase M | P14384 | SRM |
| 14 | CTSD      | Cathepsin D | P07339 | SRM |
| 15 | ECM1      | Extracellular matrix protein 1 | Q16610 | ELISA, SRM |
| 16 | EFNA5     | Ephrin-A5 | P52803 | SRM |
| 17 | F5        | Coagulation factor V | P12259 | SRM |
| 18 | FAM3D     | Protein FAM3D | Q96BQ1 | ELISA |
| 19 | GALNTL4   | Putative polypeptide N-acetylgalactosaminyltransferase-like protein 4 | Q6P9A2 | SRM |
| 20 | GOLPH2    | Golgi phosphoprotein 2 | Q8NBJ4 | SRM |
| 21 | GRN       | Granulins | P28799 | ELISA |
| 22 | GSPT1     | Eucariotic peptide chain release factor GTP-binding subunit ERF3A | P15170 | SRM |

TABLE 3-continued

List of 43 serum glycoproteins measured in human sera

| | Gene name | Protein name | Accession number | Technique used for analysis |
|---|---|---|---|---|
| 23 | HYOU1 | Hypoxia up-regulated protein 1 | Q9Y4L1 | SRM |
| 24 | KIT | Mast/stem cell growth factor receptor | P10721 | SRM |
| 25 | KLK3 | Prostate-specific antigen | P07288 | ELISA, SRM |
| 26 | L1CAM | Neural cell adhesion molecule L1 | P32004 | SRM |
| 27 | LGALS3BP | Galectin-3-binding protein | Q08380 | ELISA, SRM |
| 28 | LOX | Protein-lysine 6-oxidase | P28300 | SRM |
| 29 | LRP1 | Prolow-density lipoprotein receptor-related protein 1 | Q07954 | SRM |
| 30 | MME | Neprilysin | P08473 | ELISA |
| 31 | MMP1 | Interstitial collagenase | P03956 | SRM |
| 32 | NCAM1 | Neural cell adhesion molecule 1 | P13591 | SRM |
| 33 | OLFM4 | Olfactomedin-4 | Q6UX06 | SRM |
| 34 | PGCP | Plasma glutamate carboxypeptidase | Q9Y646 | SRM |
| 35 | PIGR | Polymeric immunoglobulin receptor | P01833 | ELISA |
| 36 | POSTN | Periostin | Q15063 | ELISA |
| 37 | PSAP | Proactivator polypeptide | P07602 | SRM |
| 38 | SEMA4D | Semaphorin-4D | Q92854 | SRM |
| 39 | TFRC | Transferrin receptor protein 1 | P02786 | SRM |
| 40 | THBS1 | Thrombospondin-1 | P07996 | ELISA, SRM |
| 41 | TIMP1 | Metalloproteinase inhibitor 1 | P01033 | ELISA, SRM |
| 42 | TM9SF3 | TM9SF3 protein | Q8WUB5 | SRM |
| 43 | VTN | Vitronectin | P04004 | SRM |
| 44 | ICAM1 | Intercellular adhesion molecule 1 | P05362 | SRM |
| 45 | CPE | Carboxypeptidase E | P16870 | ELISA |
| 46 | MSMB | Beta-microseminoprotein | P08118 | ELISA |

Table 3: List of 46 serum glycoproteins measured in human sera. The selected biomarker candidates were either analyzed by SRM or ELISA. Gene name, Protein name (shortened) and Accession number are defined as given in Table 1.

Statistical Analysis

Following statistical analysis, we could identify a 3-biomarker signature comprising of Asporin (ASPN), Vitronectin (VTN) and Membrane copper amine oxidase (AOC3). The Signature had an accuracy of 81% in discriminating between BPH (n=15) and locPCa (n=16) patients; this means that 81% of the patients analyzed were correctly diagnosed by our 3-biomarker signature. AOC3 was found to be the weakest contributor. Thus we substituted this protein with other potential biomarkers and kept the ones gaining similar or higher accuracy (≥80%). The following proteins could be individually added in this way: LOX, PGCP, PSAP, THBS1 (FIG. 3 A).

The discrimination of PSA itself was measured as well which resulted in an accuracy of 71% discriminating between BPH (n=15) and locPCa (n=16) patients.

Additionally, we added PSA data to the core signature of ASPN and VTN. By including one of the following proteins: AOC3, CFH, CLU, KIT, LOX, TFRC, THBS1, LGALS3BP, GOLPH2, accuracies of up to 90% was achieved (FIG. 3 B).

Following statistical analysis using more data, we could further identify a 5-biomarker signature comprising of Asporin (ASPN), Cathepsin D (CTSD), Hypoxia up-regulated protein 1 (HYOU1) and Olfactomedin-4 (OLFM4). The Signature had an accuracy of 87% in discriminating between BPH (n=35) and locPCa (n=41) patients; this means that 87% of the patients analyzed were correctly diagnosed by our 5-biomarker signature. The discrimination of PSA itself was measured as well which resulted in an accuracy of 72% discriminating between BPH (n=41) and locPCa (n=64) patients (FIG. 3C).

Additionally, by removing in each case only one of these four proteins an accuracy of up to 83% was achieved (FIG. 3C).

Using the same dataset and applying a somewhat less stringent criterion for selection out of the systems according to table 3, a refined list of biomarkers was determined and is collected in table 4. An assay with a group of at least three of the systems given in table 4 in combination with a PSA (ELISA) measurement leads to an accuracy of around 80% or even higher. A selection of at least four of the systems given in table 4 in combination with a PSA (ELISA) measurement even leads to an accuracy of around 85% or higher.

The threshold values for each of the systems given in table 4 indicates the concentration threshold above or below (as indicated) which a positive diagnosis can be issued. If all of the markers in one assay (for example in a group of 3 biomarkers selected from table 4) exceed in concentration above these concentration values a positive diagnosis can be issued with the accuracies as given above.

TABLE 4

List of 15 serum glycoproteins measured in human sera

| | Gene name | Protein name | Accession number | Technique used for analysis | basic conc | preferred conc |
|---|---|---|---|---|---|---|
| 1 | AKAP13 | A-kinase anchor protein 13 | Q12802 | SRM | >2500 | >2800 |
| 2 | ASPN | Asporin | Q9BXN1 | SRM | >55 | >60 |
| 3 | CFH | Complement factor H | P08603 | SRM | <250000 | <231500 |
| 4 | CP | Ceruloplasmin | P00450 | SRM | <120000 | <101500 |
| 5 | CPE | Carboxypeptidase E | P16870 | ELISA | >0.05 (OD) | >0.075 (OD) |

TABLE 4-continued

List of 15 serum glycoproteins measured in human sera

| | Gene name | Protein name | Accession number | Technique used for analysis | basic conc | preferred conc |
|---|---|---|---|---|---|---|
| 6 | CPM | Carboxypeptidase M | P14384 | SRM | <110 | <95 |
| 7 | CTSD | Cathepsin D | P07339 | SRM | <32 | <25 |
| 8 | HYOU1 | Hypoxia up-regulated protein 1 | Q9Y4L1 | SRM | >35 | >40 |
| 9 | ICAM1 | Intercellular adhesion molecule 1 | P05362 | SRM | <360 | <340 |
| 10 | LGALS3BP | Galectin-3-binding protein | Q08380 | SRM | <400 | <390 |
| 11 | MSMB | Beta-microseminoprotein | P08118 | ELISA | >0.12 (OD) | >0.15 (OD) |
| 12 | OLFM4 | Olfactomedin-4 | Q6UX06 | SRM | <20 | <15 |
| 13 | TM9SF3 | TM9SF3 protein | Q8WUB5 | SRM | >8 | >10 |
| 14 | VTN | Vitronectin | P04004 | SRM | <3500 | <3300 |
| 15 | GALNTL4 | Putative polypeptide N-acetylgalactosaminyltransferase-like protein 4 | Q6P9A2 | SRM | <15 | <10 |

Table 4: Refined list of 15 serum glycoproteins measured in human sera after statistical analysis (BPH (n = 35) and locPCa (n = 41)). Gene name, Protein name (shortened) and Accession number are defined as given in Table 1. In a first column the basic concentration threshold values in ng/ml are given, and in a second column the preferred concentration threshold in ng/ml values are given. Where OD is indicated measurement takes place at 405 nm and relative values are given using commercially available antibodies (CPE: R&Dsystems, polyclonal: Nr. AF3587 and R&Dsystems, monoclonal: MAB3587; MSMB: R&Dsystems, polyclonal: Nr. AF3780 and Abnova, monoclonal: H00004477-M08).

b) Using a biomarker signature comprising of the following biomarkers: Asporin (ASPN), Vitronectin (VTN), Cathepsin D (CSTD), Polypeptide N-acetyl-galactosaminyltransferase GALNTL4, Proactivator polypeptide (PSAP), and Thrombospondin-1 (THBS-1), we could correctly distinguish between locPCa (n=16) and metPCa (n=21) patients in 100% of the cases. PSAP was found to be the weakest contributor. Leaving it out, still 97% accuracy in the discriminant analysis was achieved. Thus we substituted this protein with other potential biomarkers and kept the ones ameliorating the accuracy (>97%). The following protein could be individually added in this way: CEACAM1, EFNA5, GSPT1, HYOU1, KIT (all gaining an accuracy of 100%) (FIG. 3).

It should be noted that any of the systems as given in table 3, preferably at the combination of two, most preferably as a combination of at least three (or exactly 3), of at least four (or exactly 4) or of at least five (or exactly 5) glycoproteins can be an assay which shall be covered by the present invention. The specific statistically evaluated systems as outlined above are just those which for the diagnostic aspects addressed in these statistical tests could be shown to be most powerful. For different diagnostic/prognostic/therapeutic aspects or using different statistical evaluation methods, different combinations might also be possible and shall be regarded as according to the present invention.

The invention claimed is:

1. A method for therapy of prostate cancer of a subject comprising the following steps:
    a first step of measuring the concentrations of all of the following three proteins ICAM1, CTSD as well as OLFM4, or in each case fragments thereof in serum, plasma, or blood isolated from the subject, wherein said measuring is performed by contacting the serum, plasma, or blood with an affinity reagent for each protein and detecting whether binding occurs between said proteins and said affinity reagent using a quantitative readout;
    a second step of correlating the concentration of said proteins measured in said first step with a predetermined prostate cancer threshold concentration value for each of said proteins; and
    a third step of treating said subject wherein the concentration of ICAM1 protein or fragments thereof measured in the first step is less than 340 ng/ml, the concentration of CTSD protein or fragments thereof measured in the first step is less than 32 ng/ml, and the concentration of OLFM4 protein or fragments thereof measured in the first step is less than 20 ng/ml.

2. The method according to claim 1, wherein said measuring is carried out using at least one technique selected from the group consisting of selected reaction monitoring (SRM), selected reaction monitoring (SRM) in combination with liquid chromatography and enzyme-linked immunosorbent assays (ELISA).

3. The method according to claim 1, wherein the affinity reagent is an antibody.

4. The method according to claim 1, wherein the quantitative readout is provided by an enzyme linked immunosorbent assay (ELISA).

5. A method for therapy of localized prostate cancer of a subject comprising the following steps:
    a first step of measuring the concentrations of all of the following three proteins ICAM1, CTSD as well as OLFM4, or in each case fragments thereof in serum, plasma, or blood isolated from the subject, wherein said measuring is performed by contacting the serum, plasma, or blood with an affinity reagent for each protein and detecting whether binding occurs between said proteins and said affinity reagent using a quantitative readout;
    a second step of correlating the concentration of said proteins measured in said first step with a predetermined localized prostate cancer threshold concentration value for each of said proteins; and
    a third step of treating said subject wherein the concentration of ICAM1 protein or fragments thereof measured in the first step is less than 340 ng/ml, the concentration of CTSD protein or fragments thereof measured in the first step is less than 25 ng/ml, and the concentration of OLFM4 protein or fragments thereof measured in the first step is less than 15 ng/ml.

6. The method according to claim 5, wherein the affinity reagent is an antibody.

7. The method according to claim 5, wherein the quantitative readout is provided by an enzyme linked immunosorbent assay (ELISA).

8. A method for therapy of localized prostate cancer of a subject involving the following steps:
- a first step of measuring the concentrations of all of the following three proteins ICAM1, CTSD as well as OLFM4, or in each case fragments thereof in serum, plasma, or blood isolated from the subject, wherein said measuring is performed by contacting the serum, plasma, or blood with an affinity reagent for each protein and detecting whether binding occurs between said proteins and said affinity reagent using a quantitative readout, and additionally measuring the concentration of the Prostate Specific Antigen (PSA) in the serum, plasma or blood using an affinity reagent-based assay,
- a second step of correlating the concentration of said proteins measured in said first step with a predetermined localized prostate cancer threshold concentration value for each of said proteins and correlating the concentration of the Prostate Specific Antigen measured in the affinity reagent-based assay with a predetermined threshold concentration value; and
- a third step of treating said subject wherein the concentration of ICAM1 protein or fragments thereof measured in the first step is less than 340 ng/ml, the concentration of CTSD protein or fragments thereof measured in the first step is less than 25 ng/ml, and the concentration of OLFM4 protein or fragments thereof measured in the first step is less than 15 ng/ml.

9. The method according to claim 8, wherein the affinity reagent is an antibody.

10. The method according to claim 8, wherein the affinity reagent-based assay is provided by an enzyme linked immunosorbent assay (ELISA).

11. The method according to claim 1, wherein the first step further comprises measuring the protein concentration of ASPN or fragments thereof so as to measure the protein concentrations of ASPN, ICAM1, CTSD and OLFM4, or in each case fragments thereof.

12. The method according to claim 5, wherein the first step further comprises measuring the protein concentration of ASPN or fragments thereof so as to measure the protein concentrations of ASPN, ICAM1, CTSD and OLFM4, or in each case fragments thereof.

13. The method according to claim 8, wherein the first step further comprises measuring the protein concentration of ASPN or fragments thereof so as to measure the protein concentrations of ASPN, ICAM1, CTSD and OLFM4, or in each case fragments thereof.

* * * * *